United States Patent [19]
Caspari et al.

[11] Patent Number: 5,902,321
[45] Date of Patent: May 11, 1999

[54] DEVICE AND METHOD FOR DELIVERING A CONNECTOR FOR SURGICALLY JOINING AND SECURING FLEXIBLE TISSUE REPAIR MEMBERS

[75] Inventors: Richard B. Caspari, Maidens, Va.; Alan Chervitz, Hopkinton, Mass.; Thomas Wade Fallin, Hyde Park, Utah; Rickey D. Hart, Plainville, Mass.; Daniel F. Justin, Logan; Daniel A. Perkins, Hyde Park, both of Utah

[73] Assignee: Innovasive Devices, Inc., Marlborough, Mass.

[21] Appl. No.: 08/901,027

[22] Filed: Jul. 25, 1997

[51] Int. Cl.⁶ ..................................... A61B 17/04
[52] U.S. Cl. ........................................... 606/232
[58] Field of Search ..................... 606/232, 220, 606/170, 139, 72, 104, 66, 67, 68, 73, 76–77, 148; 441/34, 43, 36–38, 59–61

[56] References Cited

U.S. PATENT DOCUMENTS

| | | |
|---|---|---|
| 5,062,846 | 11/1991 | Oh et al. . |
| 5,078,731 | 1/1992 | Hayhurst . |
| 5,100,417 | 3/1992 | Cerier et al. ............................ 606/232 |
| 5,160,339 | 11/1992 | Chen et al. . |
| 5,171,251 | 12/1992 | Bregen et al. . |
| 5,222,976 | 6/1993 | Yoon . |
| 5,234,449 | 8/1993 | Brucker et al. . |
| 5,268,001 | 12/1993 | Nicholson et al. ........................ 606/72 |
| 5,282,832 | 2/1994 | Toso et al. . |
| 5,376,101 | 12/1994 | Green et al. . |
| 5,383,905 | 1/1995 | Golds et al. . |
| 5,409,499 | 4/1995 | Yi . |
| 5,423,860 | 6/1995 | Lizardi et al. ........................... 606/232 |
| 5,474,572 | 12/1995 | Hayhurst . |
| 5,514,159 | 5/1996 | Matula et al. . |
| 5,520,702 | 5/1996 | Sauer et al. . |
| 5,531,763 | 7/1996 | Mastri et al. ........................... 606/148 |
| 5,630,824 | 5/1997 | Hart . |
| 5,649,963 | 7/1997 | McDevitt . |

FOREIGN PATENT DOCUMENTS

| | | |
|---|---|---|
| 0634142A2 | 1/1995 | European Pat. Off. . |
| 2682867 | 4/1993 | France . |
| 29613728 U1 | 8/1996 | Germany . |

*Primary Examiner*—Michael Buiz
*Assistant Examiner*—Vikki Trinh
*Attorney, Agent, or Firm*—Allen, Dyer, Doppelt, Milbrath & Gilchrist, P.A.

[57] ABSTRACT

A connector delivery device and method include a rod frangibly affixed to an inner member and a support member slidable around the rod. The support member is adapted to support an outer member for movement relative to the inner member for forming a snap fit therebetween, the snap fit for trapping flexible material such as suture at a surgical site. In an alternate embodiment a pistol-type handle and trigger operate to move a push rod seated within an outer barrel against the outer member to push the outer member over the inner member to form the snap fit. A collet is attached to a collet barrel slidable within the outer barrel, the collet barrel positioned in surrounding relation to the push rod. The collet, which is spring biased into a closed position, supports the outer member prior to activation of the delivery device.

14 Claims, 14 Drawing Sheets

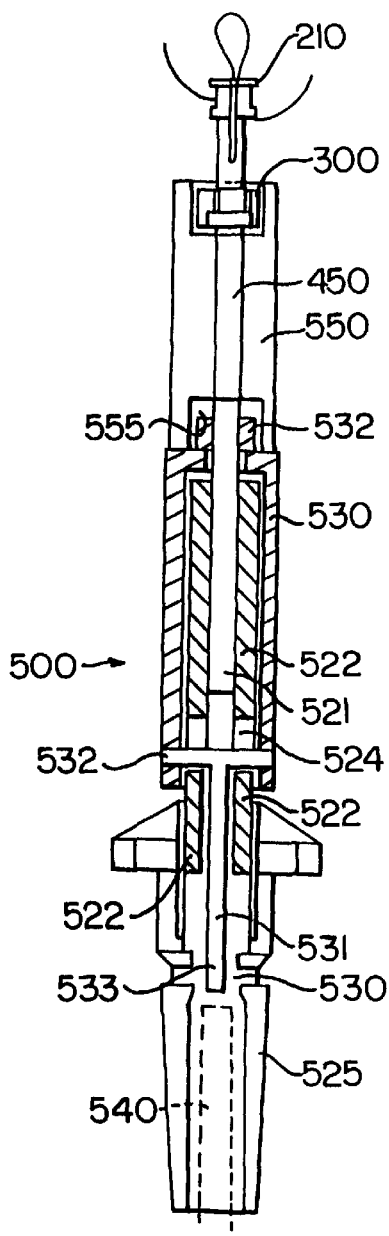
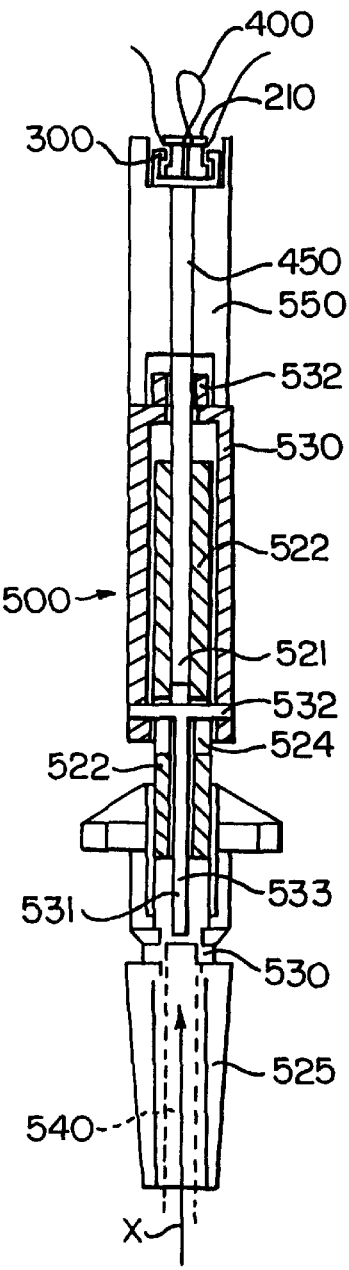
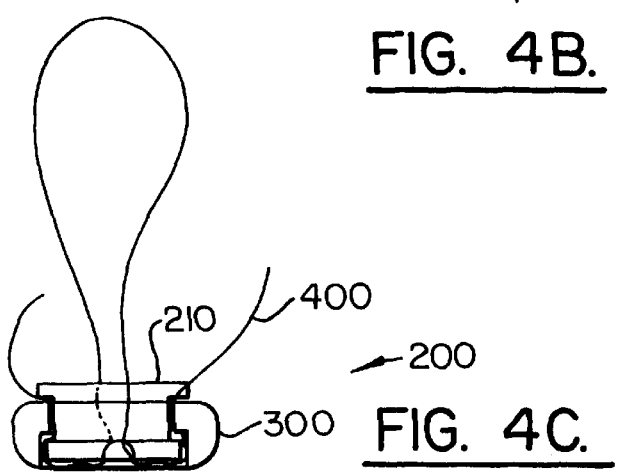

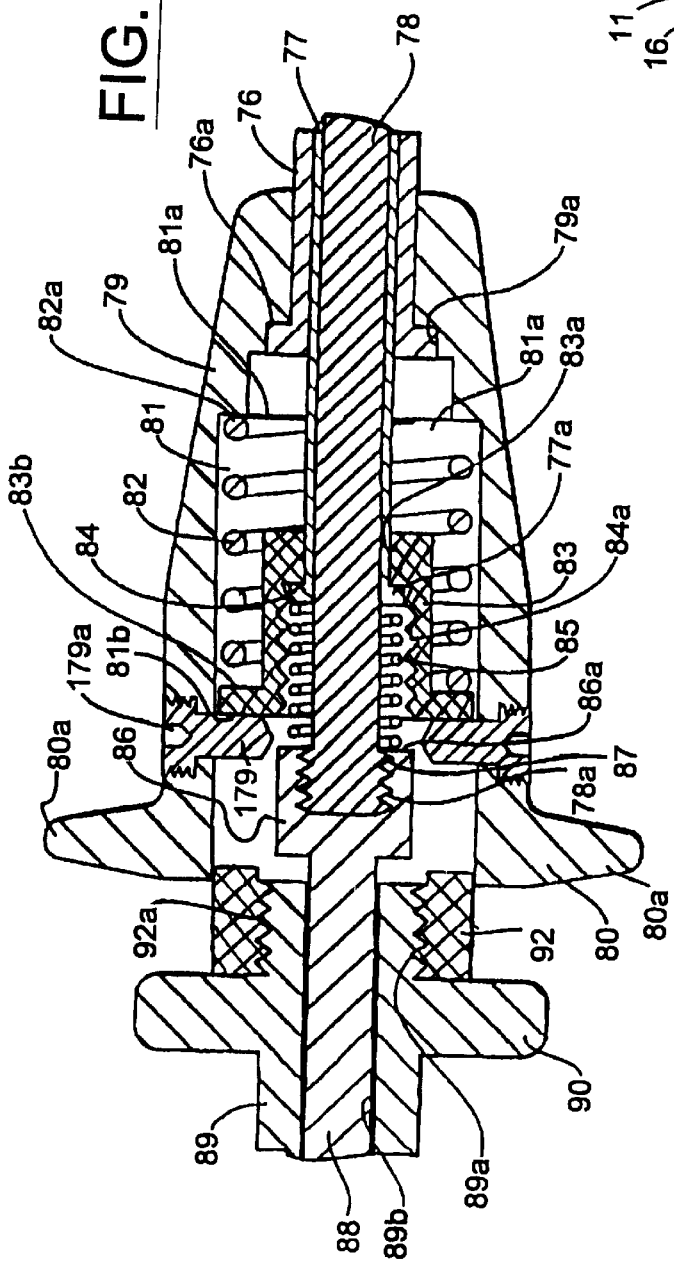
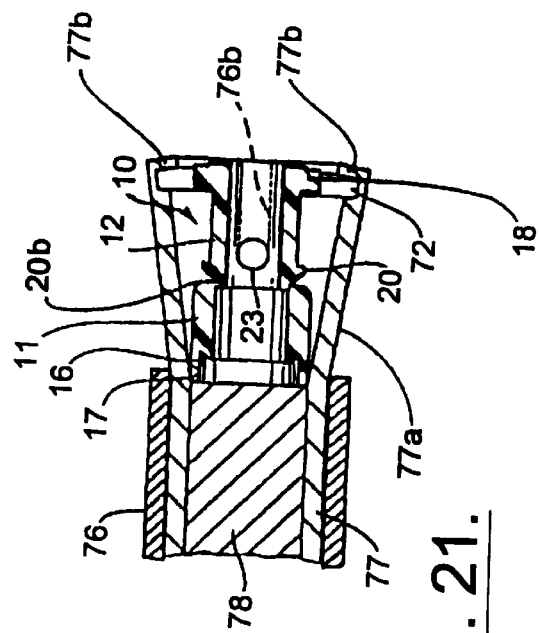

DEVICE AND METHOD FOR DELIVERING A CONNECTOR FOR SURGICALLY JOINING AND SECURING FLEXIBLE TISSUE REPAIR MEMBERS

1. Field of the Invention

This invention relates to a surgical connector and method for the tightening, joining, and securing of flexible members such as suture, cable, wire, strap, band, tissue, or any combination of flexible materials as can be joined together surgically, and in particular to devices and methods that are used to surgically connect flexible members, which may be both ends of a same member, without tying knots. The invention further relates to devices and methods for delivering such a connector.

2. Related Art

With the advent of endoscopic surgical techniques such as arthroscopy, laparoscopy, gastroentroscopy, and laryngoscopy, surgeons are able to access, visualize, and operate on surgical sites from new perspectives. Endoscopic, laparoscopic, and arthroscopic surgery relies on small-diameter cannulas that extend through small incisions made through the skin into a surgical site. In an endoscopic procedure, a video camera having a small-diameter lens is inserted through a trocar tube that is passed through an incision and permits visual inspection and magnification of the surgical site. Small-diameter flexible instruments can then be manipulated to the repair site through additional cannulas. These instruments permit the surgeon to precisely prepare the tissue that is to be repaired or joined together. However, with few exceptions, such as tissue staples or laser fusion tissue is still repaired by stitching with suture.

Currently, an effective and often-used method of surgically tightening and joining suture or other flexible tissue repair members together is by tying knots. Various devices have been developed to assist the surgeon in tying knots during surgical procedures, including suture and surgical clip-type devices that may, however, be too large to use in the confined space available in an endoscopic procedure. Such suture clip and surgical clip devices generally include one-piece bendable arrangements having hinged mechanisms where two ends thereof are brought together to enclose the suture and are locked thereto. Examples of such devices are shown in U.S. Pat. Nos. 5,474,572 to Hayhurst; 5,409,499 to Yo; 5,330,442 to Green et al.; 5,234,449 to Bruker et al.; 5,171,251 to Bregen et al.; 5,160,339 to Chen et al.; 5,078,731 to Hayhurst; and 5,062,846 to Oh. Additional, a number of nonhinged suture locking devices have been developed, such as U.S. Pat. Nos. 5,413,585 to Pagedas; 5,282,832 to Toso et al.; 5,376,101 to Green et al.; 4,505,274 to Speelman; and 3,910,281 to Kletschka et al. None of these devices, however, addresses in-line tensioning and the joining of a flexible member in the same line. By providing for such in-line tensioning and joining of the flexible members, a tighter, more secure fastening of the tissue would be provided that is preferable for use endoscopically.

For use in endoscopy and like procedures, devices such as knot pushers have been designed to assist in tying knots endoscopically. Examples of such devices designed to assist with arthroscopic knot tying include commercially available knot pushers such as disclosed in U.S. Pat. Nos. 5,217,471 to Burkhart and 5,562,684 to Kammerer. In a utilization of each of these devices, the tissue is temporarily held together with instruments, and sutures keep the tissue together, as by pulling the suture ends tight and tying them together with knots. After tying, the sutures extend from the suturing site through the cannula. The exposed free ends of the sutures are then tied loosely outside the cannula, with the loose knot then pushed through the cannula using a knot pusher to the repair site. This procedure is then repeated until the knot is tight and the tissue is securely joined.

In endoscopic surgery, even with these devices, knot tying is time consuming, difficult, and may produce a knot or knots that lack adequate holding strength or tightness. Accordingly, although conventional knot-tying methods may be adequate for open surgical procedures where the suture can be pulled, as with direct in-line access and visualization, and even where the flexible members or both ends of the same member can be joined with tightly applied knots, it is not necessarily optimal to join flexible members together with knots during endoscopic procedures. Due to the dimensional constraints of endoscopy, knots tied through cannulas tend not to be as tight as knots tied through open surgical techniques. Also, because the surgical sites tend to be smaller in endoscopic procedures than in open procedures, multiple knot throws are often needed to secure the knots. Accordingly, endoscopic knots tend to be significantly proportionately larger than knots tied during open procedures with respect to a small surgical site. This combination of a formation of a relatively large, loose knot in a small hard-to-access surgical site introduces potential surgical difficulties that may affect the procedure outcome. Additionally, such knot-tying procedures can be time consuming and may require advanced endoscopic technical experience to effectively join the tissue together tightly. Also, it is desirable to provide a knot having a verifiable hold. Thus a device that securely, efficiently, and effectively joins together two or more ends of flexible tissue repair members as used in soft tissue repair, such as a suture, is needed during both open and endoscopic procedures.

In addition to the above, the issue of joining suture together endoscopically without the use of knots has been addressed. U.S. Pat. No. 5,630,824 to Hart teaches a suture attachment device wherein a base element has an axial passage for receiving one or more suture filaments. The base element is frangibly attached to a locking element that is adapted for movement into the axial passage, in which position the suture filaments are trapped therein. U.S. Pat. No. 5,520,702 to Sauer et al. provides a method and apparatus that attempts to overcome the difficulty of endoscopically joining sutures together. The Sauer et al. apparatus teaches a deforming member that connects to a securing member by plastically deforming around the suture, holding it together. Additionally, U.S. Pat. No. 5,514,159 to Matula et al. describes a guillotine suture clip that joins together sutures by a mechanical means. This suture retainer joins the suture ends together in a direction that is transverse to the joined sutures. Installation of this device, therefore, requires an engagement force that is applied across or is different from the line of the suture. Thus endoscopic engagement of the Matula et al. device, as described, could be potentially complicated. Further, U.S. Pat. No. 5,383,905 to Golds et al. describes a two-piece suture locking device that is arranged to tie off a suture that is looped about tissue. The device provides for tightening the suture in line with the direction the suture is pulled during tightening. However, the design also limits the joining of the suture such that it will also be in line with and in the direction of the applied tension. Also, the design of the Golds et al. device does not permit additional tightening of the suture, as the two pieces of the device connect when engaged to join the suture, prohibiting future suture tightening.

The above examples relate mainly to the joining of sutures endoscopically, although it should be understood that it would be desirable to provide a device that surgically joins together other flexible members such as cable, wire, bands, or other flexible members used to join tissue together. A number of such devices are currently available, with an example disclosed in U.S. Pat. No. 4,050,464 to Hall. Joining such flexible members has, however, heretofore involved wrapping the flexible members around bone fragments or passing them through bone fractures and then tightening them to pull the fractures together. After tightening, the loose ends are then either tied, twisted, or crimped together with crimping devices. These devices and methods for joining result in connections that may exhibit varying strengths or purchase due to the variations in the deformation of the connector material. Accordingly, it was recognized that a device and method for holding two or more ends of cable, wire, or bands together by a reliable mechanical means that does not completely depend on plastic deformation of the material is needed.

Heretofore, surgeons have lacked the ability to join together two or more dissimilar flexible members where a use of knots for such joining has not been possible due to different mechanical and physical properties of the flexible members, or where space has not been available, or where needed crimps or clips have not been available to join flexible members having different properties. A device that is specifically designed to join together different types of flexible members could therefore potentially open new areas of surgical procedures. With such a device, a surgeon could then repair a soft tissue, such as ligament, with suture and repair a harder tissue, such as bone, with a more rigid band. Accordingly, it is recognized that a device that could then join together the two flexible members of different properties would be an asset to the surgical community.

Additionally, it is further recognized that it would be desirable directly to join together flexible tissue, such as ligaments. Where earlier surgical staples and clips have been developed for such purposes, as, for example, the devices shown in U.S. Pat. Nos. 4,505,273 to Braun and 5,222,975 to Crainich, such have not been practical for reliably joining such flexible tissue. Alternatives to suture for joining tissue are shown in U.S. Pat. No. 4,955,913 to Robinson, which shows one-piece looped devices, with like devices shown in U.S. Pat. Nos. 5,222,976 to Yoon and 5,123,913 to Wilk et al. None of these devices, however, is suitable for joining tissue by means of mechanical fastening. Heretofore, as needed, ends of ruptured long flexible tissue, such as ligaments, have been temporarily joined together, typically by a mechanical means, until the tissue heals biologically.

Heretofore, various devices have been developed that have attempted to overcome the disadvantages of conventional suture and knots. Such have included staples, clips, clamps, or other fasteners. Additionally, it has been attempted to join tissue using suture during endoscopic surgery, such as by cinching or crimping suture ends or segments together. No device or method has been known that combines the following three functions: in-line tightening of the flexible member prior to joining; a change in the direction of the flexible member during and after joining; and a capability for additional tightening of the flexible member during joining.

SUMMARY OF THE INVENTION

It is a principal object of the present invention to provide a device for use in an endoscopic procedure that will allow for an in-line joining and tightening of one or more flexible members and that will further permit the flexible member(s) to be additionally tightened, as needed, as the device is engaged.

Another object of the present invention is to provide a device that is capable of joining sections of tissue to be noncollinear with a tension on a flexible member, providing for a mechanically stable engagement.

A further object of the present invention is to provide a device comprising inner and outer members arranged such that an inner member will allow a flexible member to pass in line through its center, during tightening, with an outer member having an inside surface commensurate with that of the inner member outside surface so as to be pushed thereover to lock the flexible member between the inner and outer member opposing or shared surfaces.

An additional object of the present invention is to provide such a device that is releasable from the flexible material without damage thereto if it is desired to reverse or remake the connection.

Yet another object of the present invention is to provide for joining a plurality of flexible members that may be alike or physically different, and where each member is passed through the center of an inner member and are, individually or together, passed back between the opposing or shared surfaces of the inner and outer members.

Still another object of the present invention is to provide a device whose component inner and outer members can be fabricated as a single unit and adapted to conveniently break away from one another and for locking together to capture a flexible member between opposing or shared surfaces.

Still another object of the present invention is to provide an instrument for delivery of the device and a method for its use to join flexible members in an endoscopic surgical procedure where the instrument will hold the respective device inner and outer members in position as a flexible member is passed through the center of the inner member, and will maintain the relative positioning of the members as they slide along the length of the flexible members to where, operating the instrument, the outer member is fitted to the inner member, to lock the device to the flexible members.

Still another object of the present invention is to provide an instrument arranged to maintain the relative position of the device members to the instrument tip during travel along flexible members to a site where the flexible members are connected, whereat the flexible members above the joint are cut.

Still another object of the present invention is to provide a device and an instrument for delivering the device that are easily and conveniently used in an endoscopic surgical procedure for permanently joining flexible members together.

The present invention has particular application to the surgical joining of flexible members, such as sutures, that may comprise one piece of material, both ends of the same member, or a plurality of flexible pieces. Securing of flexible pieces of material, such as cable and wire, is possible without twisting or joining the pieces together or using crimps. It is possible to secure more than two strands of the same flexible material or both ends of the same member during a suture stitching procedure, and also to directly join flexible bodily tissues.

Another application is for affixing a single piece of flexible material at a desired site during a surgical procedure, particularly an endoscopic procedure.

A particular advantage of the present invention is that the connector is applied in the direction of the suture route, rather than transverse to it, and a lower-profile connector is provided. This feature is particularly useful in endoscopy, where space is limited.

These and other objects are achieved by the connector and driver of the present invention, which obviate the need for tying knots or forming a permanent connection such as a crimp. In a preferred embodiment, the connector comprises an outer member that has a longitudinal bore at least partially therethrough extending from the top end. The connector further comprises an inner member a portion of which is dimensioned to fit within the bore and also has a passage extending from the top end to an exit portal. Means are provided for retaining at least a portion of the inner member within the outer member bore when the inner member is moved from an open position wherein the exit portal is exposed and a locked position wherein the exit portal is substantially blocked by the outer member.

In the locked position, at least one piece of elongated flexible material is passed through the inner member passage from the top end and out the exit portal. The material is forced to proceed along a serpentine path from the portal upward between the outer wall of the inner member and the inner wall of the outer member bore, which are closely opposed. The material then emerges from the top of the outer member bore.

The serpentine pathway defined by the material enhances the strength of the connection, which is particularly effective in the case of suture material, which is known to slip easily. The snap fit achieves a connection in line with the material, which permits a longitudinal force to be used in forming the connection. This is particularly advantageous in endoscopic applications, where space is limited. Also, attachments that require securing by a perpendicular approach would necessitate an additional tool and incision.

The snap fit further creates an additional tightening force during the forming of the connection, since the material pathway is lengthened during the mating between the inner and outer members.

The piece of material to be secured may include one or more pieces of suture or a loop of suture having two ends, although this is not intended as a limitation. The connector is also usable for securing sections of wire or cable.

Another important feature of the present invention is the reversible nature of the snap fit. If the user wishes to release the connection, the inner member is movable out of the outer member bore by application of sufficient force in an upward direction. Such a force may be applied, for example, by pulling on the end(s) of suture material axially downward, which causes the suture material to exert a downward force on the outer member and an upward force on the inner member.

The inner member is adapted to allow the flexible material to pass in line during tightening. So arranged, the inner member is free to move along the flexible member and therefore can be moved into direct contact with a section of tissue, bone, or the like.

Further, in another embodiment of the invention, the inner and outer members are fabricated as a single unit, providing for easier loading onto one embodiment of the delivery instrument and stability of the flexible member as it is fitted and travels within the device. When the device is engaged, the connection between the inner and outer members will be broken, and the members function as in the other embodiments.

The invention also includes a delivery instrument and method for its use to allow for the delivery of the device to a body site and to be operated to join flexible members surgically. The instrument is designed to hold the inner and outer members securely while the flexible member is passed through the center of the inner member.

One instrument embodiment provides a securing arrangement for holding the outer member in a support member. The inner member is frangibly affixed to a rod that passes through the support member. A relative movement of the rod and support member permits the engagement of the inner and outer members to form a snap fit connection.

In a second embodiment the inner member is held in the instrument tip end by an interlocking connection, and the flexible member is held securely while the inner member and outer member are longitudinally slid along the length of the flexible members.

In a third instrument embodiment, the securing arrangement provides for maintaining both the inner and outer members in position in the instrument tip end and utilizes an encapsulating tubular member maintained in a barrel portion of the instrument. This instrument provides for holding the inner and outer members in the instrument tip end by an application of a physical bond that can be cemented or mechanical bone, but preferably includes molding the inner member to a push rod end to break away after the outer member is slid thereover.

The delivery instruments of the invention can also include an arrangement for connecting the flexible members to the inner and outer member. One embodiment of the connecting arrangement includes a use of one or more flexible member passers that are, in turn, loaded to travel along the desired path of the flexible material. In another delivery instrument embodiment, the connecting arrangement is a routing instrument that is connected to the delivery instrument and is arranged to force the flexible member to follow only one path through the inner and outer members.

BRIEF DESCRIPTION OF THE DRAWINGS

FIG. 4 is a longitudinal cross-sectional view of a first embodiment of the driver and the connector of FIG. 1 operating to achieve a connection of two pieces of suture. FIG. 4A shows the driver and connector prior to insertion into the surgical site. FIG. 4B shows the driver achieving the snap fit connection. FIG. 4C shows the connector in place, broken away from the driver, retaining the two suture ends in place.

FIG. 20 is an enlarged view taken along the line 20—20 of FIG. 19 of the body of the second embodiment of the delivery instrument.

FIG. 21 is an enlarged sectional view taken within the line 21—21 of FIG. 19, showing the barrel end of the instrument containing the connecting device of FIG. 11.

DETAILED DESCRIPTION OF THE PREFERRED EMBODIMENT

A description of the preferred embodiments of the present invention will now be presented with reference to FIGS. 1–21.

The connectors to be disclosed herein can be used to join together, permanently or temporarily, two or more sections of flexible materials, such as sutures, wires, cable, or the like, at a location where it is necessary to place the connected junction into a close-fitting location or against a bone surface. The connectors can also be used to secure one section of flexible material at a desired location. The materials to be connected may be physically unlike and are securely connected together by joining of members of the connecting device of the invention.

Figures 1, 2:
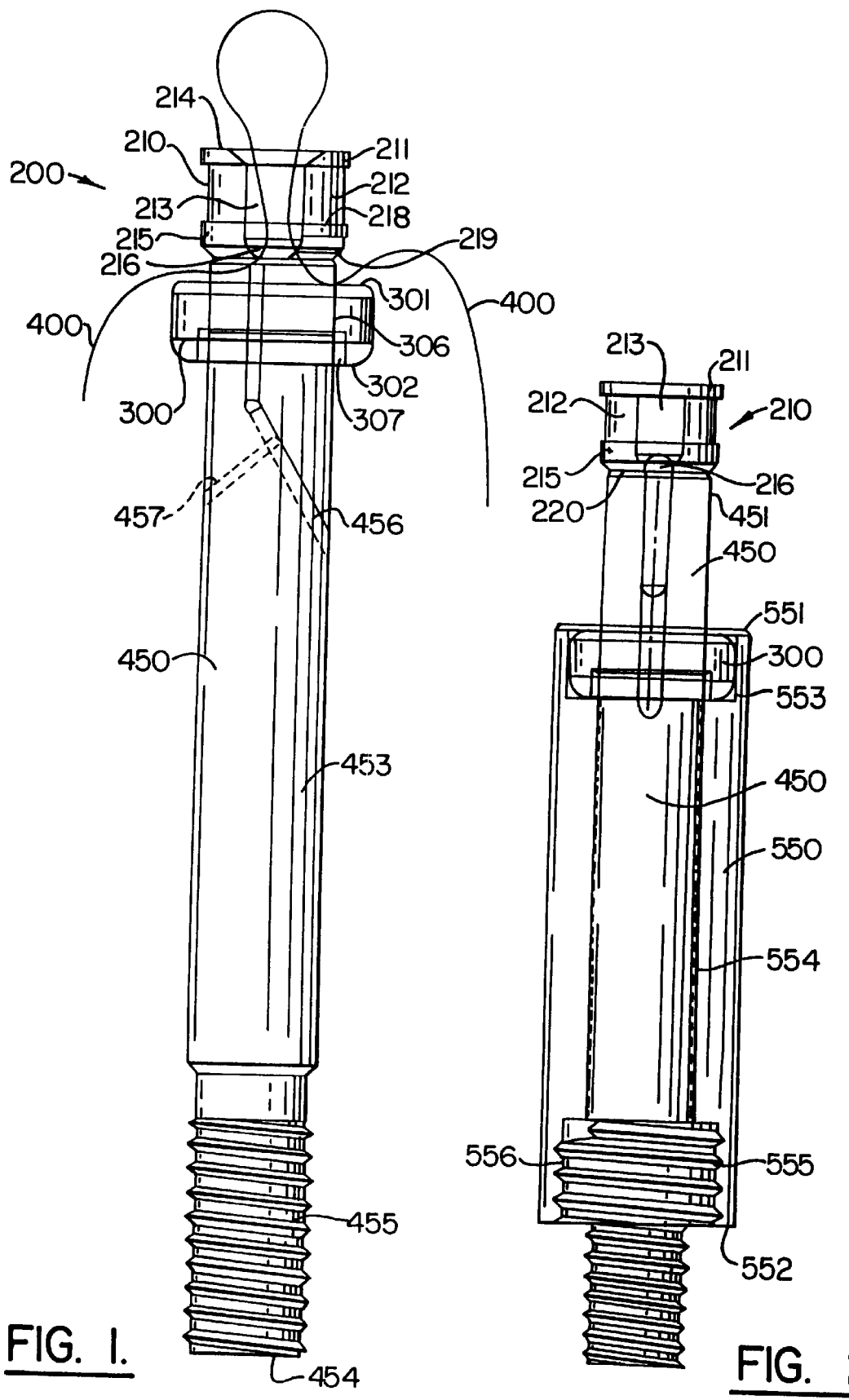
FIG. 1 is a perspective side view of a first embodiment of the connector of the present invention in the open position.
FIG. 2 is a perspective side view of an upper section the connector of FIG. 1 in the open position, rotated 90 degrees to illustrate a portal.
Figure 3:
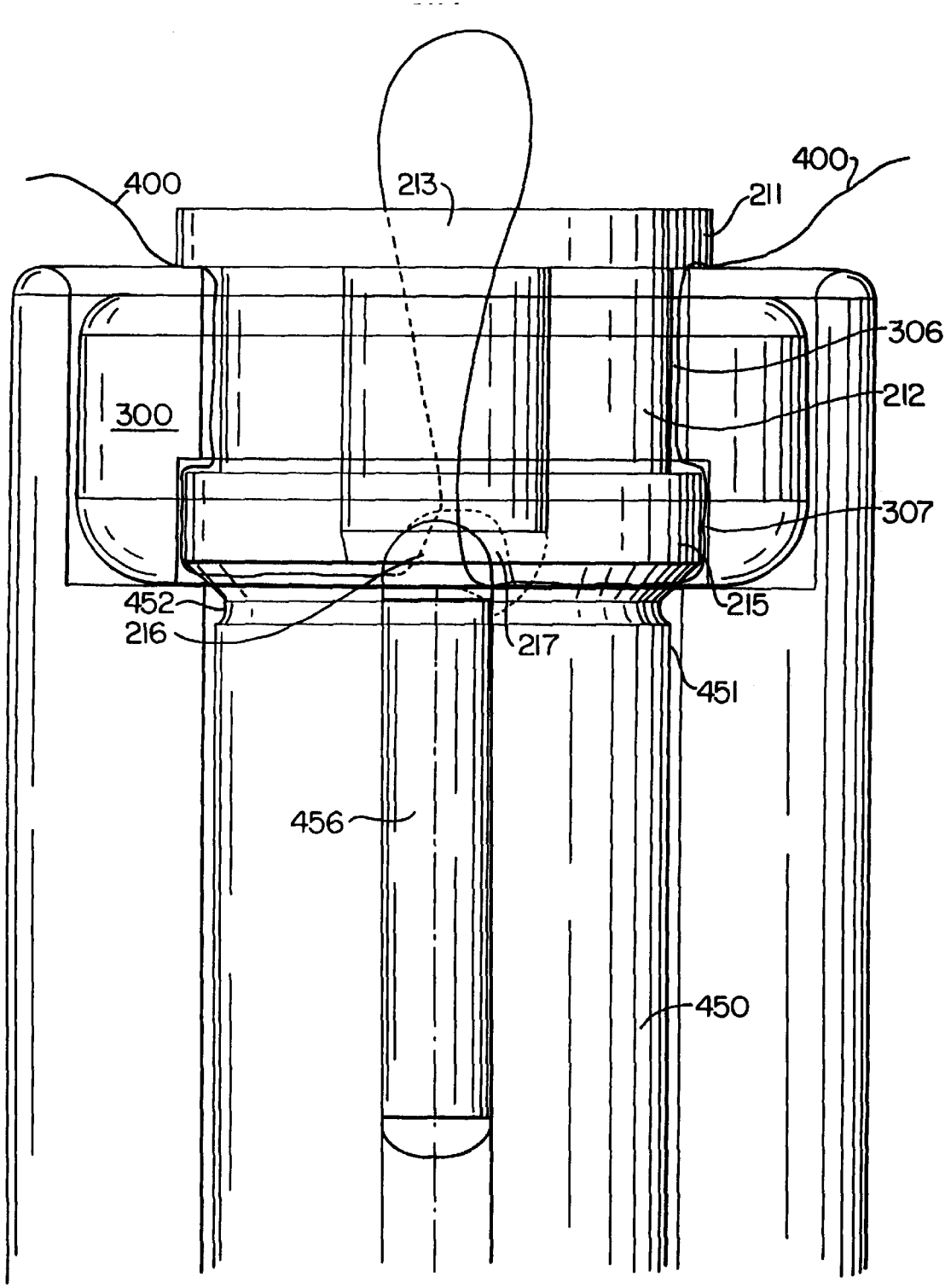
FIG. 3 is a perspective side view of the upper section of the connector of FIG. 1 in the locked position.

A first embodiment of the connector is illustrated in FIGS. 1–3. The connector 200 comprises an outer member 300 and an inner member 210, which include means for their being snap fit together. The snap fit serves to anchor one piece of flexible material, such as suture 400, in a desired location within a surgical site, or to join two or more pieces of such material without tying a knot.

The outer member 300 has a longitudinal bore at least partially therethrough. In a preferred embodiment the bore extending from a top end 301 through to a bottom end 302. In this embodiment the bore has two sections: an upper section 306 and a wider lower section 307.

The inner member 210 has a top portion 211 that includes means for preventing its passage into the outer member bore's upper section 306. In a preferred embodiment, this feature is accomplished by the top portion 211 having a diameter greater than that of the outer member bore's upper section 306.

The inner member 210 further has a central portion 212 that is adjacent and beneath the top portion 211. The central portion 212 is dimensioned to permit passage into the outer member bore's upper section 306.

The inner member 210 also has a longitudinal bore 213 that extends from a top end 214 into at least the central portion 212. This bore 213 is dimensioned to permit a passage of at least one piece of material 400 therethrough.

A distortable radial protrusion 215 is positioned adjacent and beneath the central portion 212. The protrusion 215 is dimensioned larger than at least the outer member bore's upper section 306 in a relaxed state. The protrusion 215 is distortable so as to be forcible into the outer member bore's upper section 306 in a distorted state. Preferably the protrusion 215 tapers inwardly from a top 218 to a bottom 219 thereof, which facilitates an insertion of the protrusion 215 into the outer member bore's upper section 306. The protrusion 215 is further dimensioned to fit within the outer member bore's lower section 307 in a relaxed state, and thus the protrusion's being forced through the outer member bore's upper section 306 and into the lower section 307 provides a snap fit to retain at least a portion of the inner member 210 within the outer member bore. In this position the inner member's top portion 211 and the outer member's top end 301 are closely opposed.

At least one portal, preferably two radially opposed portals 216,217, are positioned beneath the top portion 211 and extend from the inner member's side wall to the inner member's bore 213. Each portal 216,217 is dimensioned to permit the passage of at least one piece of material 400.

In FIG. 3 two pieces of material 400 are being connected and are shown to describe a serpentine path. The two pieces of material are inserted into the top of the inner member bore 213 and exit, one from each portal 216,217. The material pieces 400 then proceed between an exterior of the central portion 212 and the inner wall of the outer member's bore 306,307, and finally exit between the inner member's top portion 211 and the top end 301 of the outer member 300. This serpentine path, the retention of a portion of the inner member 210 within the outer member's bore 306,307, and the dimensioning serve to retain the two pieces 400 in a desired position.

In this first embodiment the connector 200 is placed into the snap fit position by a system including a rod 450, a support member 550, and a driver 500, which comprise additional aspects of the present invention and are shown in FIGS. 2–4C. In this embodiment the connector 200 is frangibly affixed to a rod 450 (see FIG. 1) at a position beneath the protrusion 215. The rod 450 has a diameter that is adapted to slide within the outer member's bore 306,307. The rod 450 further has means for mating with the driver 500, which is adapted to hold the inner member 210 in place relative to a movement of the outer member 300. Such a movement forces the protrusion 215 into the outer member bore, first into narrow upper section 306 and then into wider lower section 307 to form a snap fit.

The protrusion bottom 219 tapers inwardly toward the inner member's bottom end 220, where it meets the rod's top end 451. The rod's top end 451 curves inwardly and then outwardly to form a circumferential hollow 452. Where the rod 450 and inner member's bottom end 218 meet is a frangible attachment that will be seen to permit a formation of the desired connection with the aid of the rod 450, a breaking of the frangible attachment, and a removal of the rod 450, leaving the connector 200 in place.

The rod 450 further has at least one groove, here two grooves 456,457, that extend from the top end 451. The grooves 456,457 are in communication with the portals 216,217 and are dimensioned to permit the suture pieces 400 to reside therein. The grooves 456,457 facilitate loading the suture 400 onto the connector 200 prior to snap fit formation.

The rod's central portion 453 is substantially cylindrical and has a diameter adapted to closely engage the outer member bore's upper section 306. This feature is for retaining the outer member 300 in position adjacent the inner member protrusion 215 prior to snap fit formation.

In this embodiment the mating means comprises a threaded screw section 455 beneath the central portion 453 and adjacent the bottom end 454. The threaded section 455 is adapted to mate with a correspondingly dimensioned grooved portion 521 of a stationary portion of the driver 500.

The support member 550 has a longitudinal bore that extends from the top end 551 to the bottom end 552. The bore has three sections: a top section 553 adjacent the top end 551, a narrower central section 554, and a wider and grooved bottom section 555 adjacent the bottom end 552. The central section 554 has a diameter dimensioned to permit the rod 450 to slide therewithin. The top section 553 has a diameter dimensioned to permit the outer member 300 to reside at least partially therein. This recess serves to support the outer member 300 in a fixed location relative to the support member 550. Thus a sliding of the support member 550 upward relative to the rod 450, with sufficient force supplied to push the protrusion 215 through the inner member top bore section 306 and into the lower section 307, achieves a snap fit between the inner member 210 and the outer member 300.

An exemplary driver 500 for use with the device of the present invention comprises elements that cooperate to move the support member 550 while retaining the rod 450 generally stationary relative thereto. As illustrated in FIG. 4A, the driver 500 is in supporting relation to the outer member 300 and inner member 210. The support member 550 and rod 450 are loaded with/affixed to the connector elements 300 and 210, respectively, preparatory to being introduced into the surgical site. This arrangement permits the reuse of the driver 500 for multiple connections.

The rod's threaded screw section 455 is connected to the driver 500 by being screwed into a corresponding grooved section 521 of an inner cylinder 522, which has a longitudinal slot 524 running along a central portion thereof. Inner cylinder 522 is in kinetic relation with handle 525, which is retained outside the surgical site.

The grooved section 555 of the support member 550 is for mating with a correspondingly dimensioned threaded screw section 532 of a movable portion of the driver 500. Here the grooved section 555 is threaded over the threaded screw section 532, which extends above the body of outer cylinder 530, which is in surrounding relation to, but not in mechanical connection with, inner cylinder 522. Outer cylinder 530 is movable by plunger element 531, a widened portion 532 of which is in pushing relation to the outer cylinder 530. The rod portion 533 of the plunger 531 extends down from the widened portion 532 inside the inner cylinder 522 and inside the hollow area 530 of the handle 525. The rod portion 533 is in turn movable by a push rod 540 insertable into the handle hollow 530.

Thus a remote relative movement between the inner member 210 and the outer member 300 is achieved by inserting a push rod 540 into the handle hollow 530, pushing against the plunger 531, which pushes the outer cylinder 530. The outer cylinder 530 pushes the support member 550 upward, thereby also pushing the outer member 300 upward. At the same time, the handle 525 is held stationary, retaining, in turn, the rod 450 and the inner member 210 stationary. This relative motion achieves the desired snap fit at a location remote from the sites of manipulation, such as is useful in an endoscopic procedure.

An alternate embodiment of the invention, connector 10 (FIGS. 5–10), includes an outer member 11 that comprises a generally cylindrical element. The outer member 11 has an axial bore 15 therethrough and is adapted to receive a flexible inner member 12 therein. A connection of the two members relies on a deformation of at least one of the members to permit joining them together.

Figure 5:
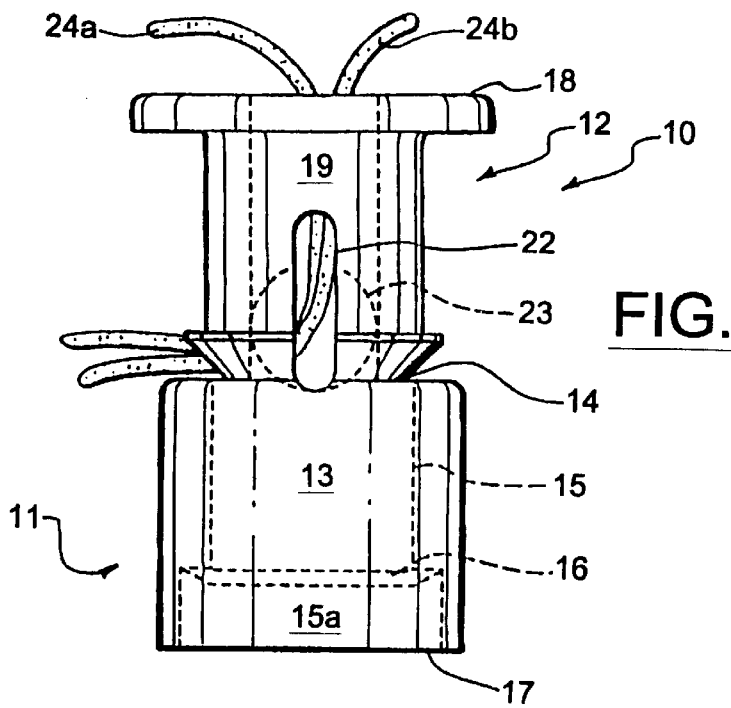
FIG. 5 is an enlarged side elevation perspective view of an inner member of a coupling device of the invention aligned for fitting longitudinally into an outer member, and showing a pair of flexible members, shown as suture, as having been passed through the inner member center and out an inner member elongate side hole, with a round side hole shown in broken lines.
Figure 6A:
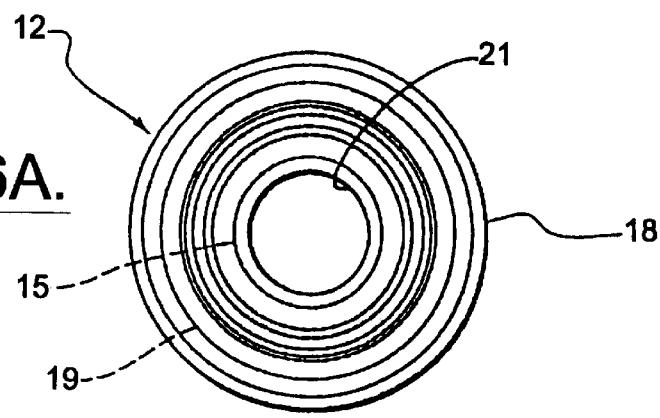
FIG. 6A is a top plan view of the aligned inner and outer members of FIG. 5.
Figure 6B:
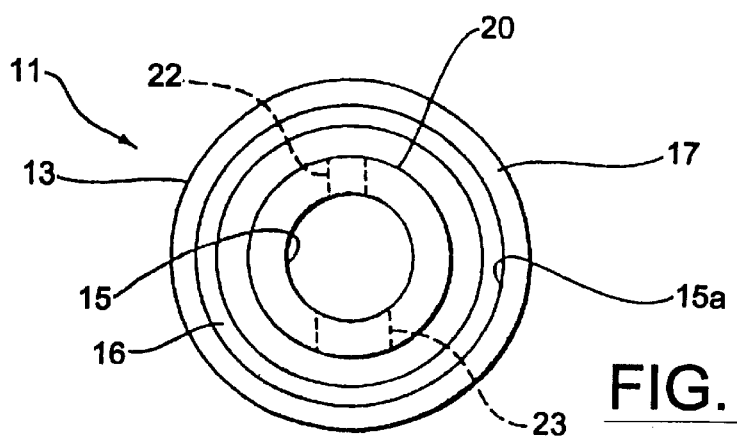
FIG. 6B is a bottom plan view of the connector of FIG. 5, with the inner member side passages shown in broken lines.

The outer member 11, as shown, has an essentially cylindrical body 13 that is open at a top end 14 and includes a generally straight longitudinal bore 15 therethrough, shown in broken lines in FIG. 5, and is stepped outwardly at a flat section 16 to form a ledge, shown in broken lines. From flat section 16, a larger generally straight bore section 15a, shown in broken lines, exits the outer member's bottom end 17.

Figure 7:
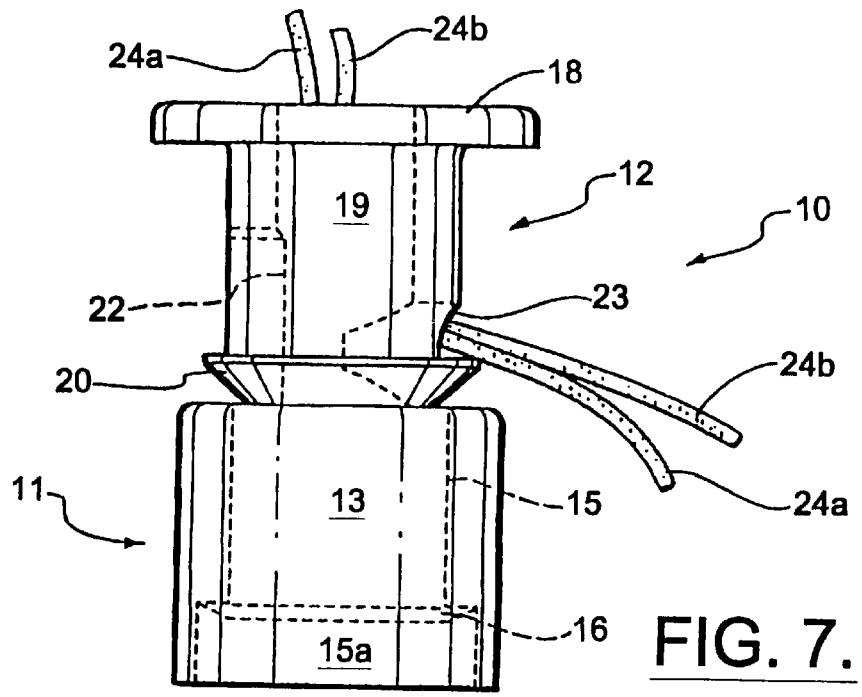
FIG. 7 is a side elevation view of the coupling device of FIG. 5, shown rotated ninety (90) degrees, showing the inner member side passages in broken lines.
Figure 8:
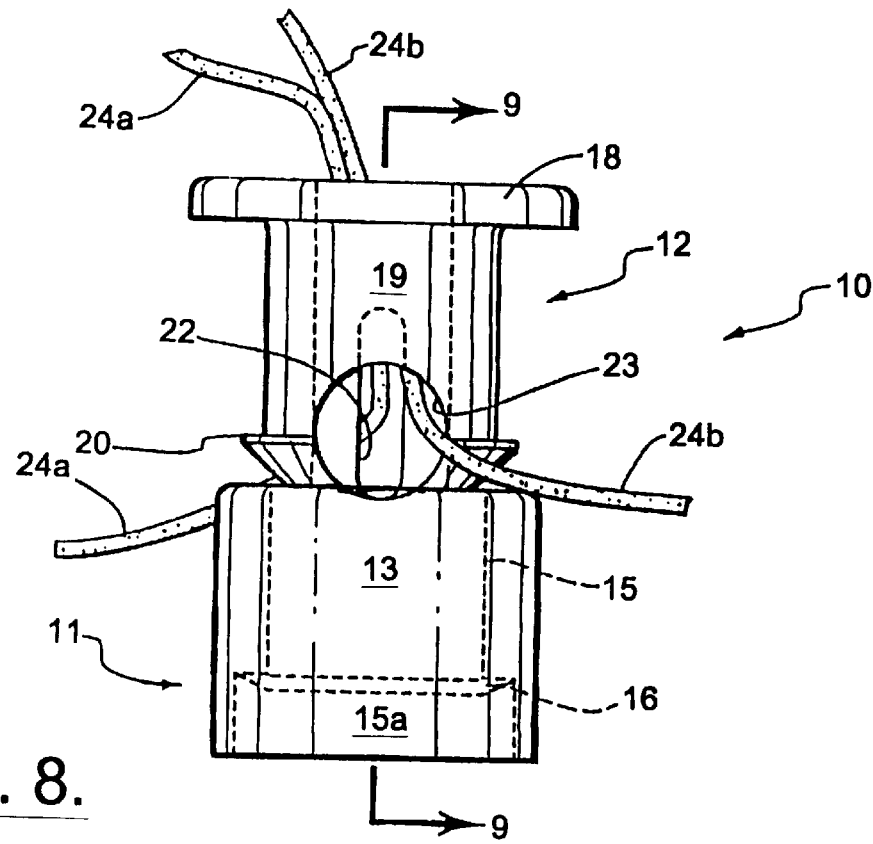
FIG. 8 is a side elevation view of the coupling device of FIG. 7, shown rotated ninety (90) degrees, where the inner member round side hole is shown in solid lines and the elongate side hole is shown in broken lines.
Figure 9:
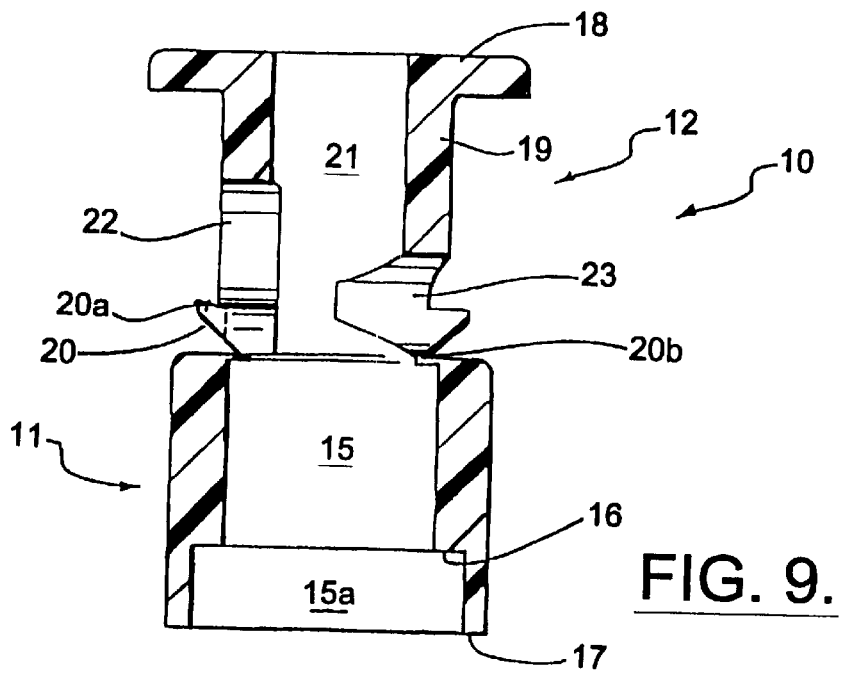
FIG. 9 is a side elevation sectional view taken along the line 9—9 of FIG. 8.

The inner member 12 has a flat portion 18 extending across a top end of a cylindrical central portion 19. The bottom portion 20 tapers inwardly, forming essentially an inverted frustrum cone 20, as shown in FIGS. 7–9. An inner member bore 21, as shown in FIG. 9, extends axially from the center of the flat top end 18 into the body 19 and, at the bottom end of the bore, intersects a pair of oppositely directed elongate and round side portals 22,23, respectively, the portal 23 shown in broken lines. Shown in FIGS. 5, 6A, and 6B, respectively, the shared or opposing surfaces of the inner member outer surface 19 and outer member bore 15 are preferably formed to have smooth cylindrical surfaces. The shared or opposing surfaces of the inner and outer members are to accommodate a piece or pieces of flexible material, shown in FIGS. 7–10, which are preferably suture or suture strands 24a,24b as having been passed through the bore 21 and are passed out of the elongate portal 22, and folded across the sloping bottom portion 20.

FIG. 7 is a view like that of FIG. 5 only showing the connector 10 as having been rotated around its longitudinal axis approximately 90° with both the elongate and round portals 22,23, respectively, shown in broken lines. FIG. 7 also shows the suture strands 24a,24b as having passed through the round portal 23, though they could as well have been fitted through the elongate portal 22. In FIG. 8, the connector 10 is shown as having again been rotated approximately 90° with the round portal 23 shown in solid lines and the elongate side hole 22 shown in broken lines. There the suture strands are shown as having been separated, with the suture strand 24a shown as having been passed out of the elongate portal 22, and the other suture strand 24b shown as having been passed out of the round portal 23.

In FIG. 9 the connector 10, as shown in FIG. 7, is shown as a side elevational sectional view of the inner and outer members connected at junction 20b and illustrating the formation of the inner and outer members as a single unit from a plastic material such as polysulfone, to exhibit plastic deformation, though it should be understood that the individual members could be formed from any biocompatible biomaterials such as metallic biomaterials, ceramic biomaterials, biocompatible polymeric materials, or the like, that are either bioabsorbable such as homopolymers, copolymers, or blended polymers of poly(L,D-lactides), polyglycolides, poly-caprolactone, or polytrimethylcarbonate; or nonbioabsorbable thermoplastic polymers such as polyetheretherketone (PEEK), polysulfone, polyethylene, or acetyl homopolymers or copolymers such as Delrin, or high-density polyurethanes can also be used.

Figure 10:
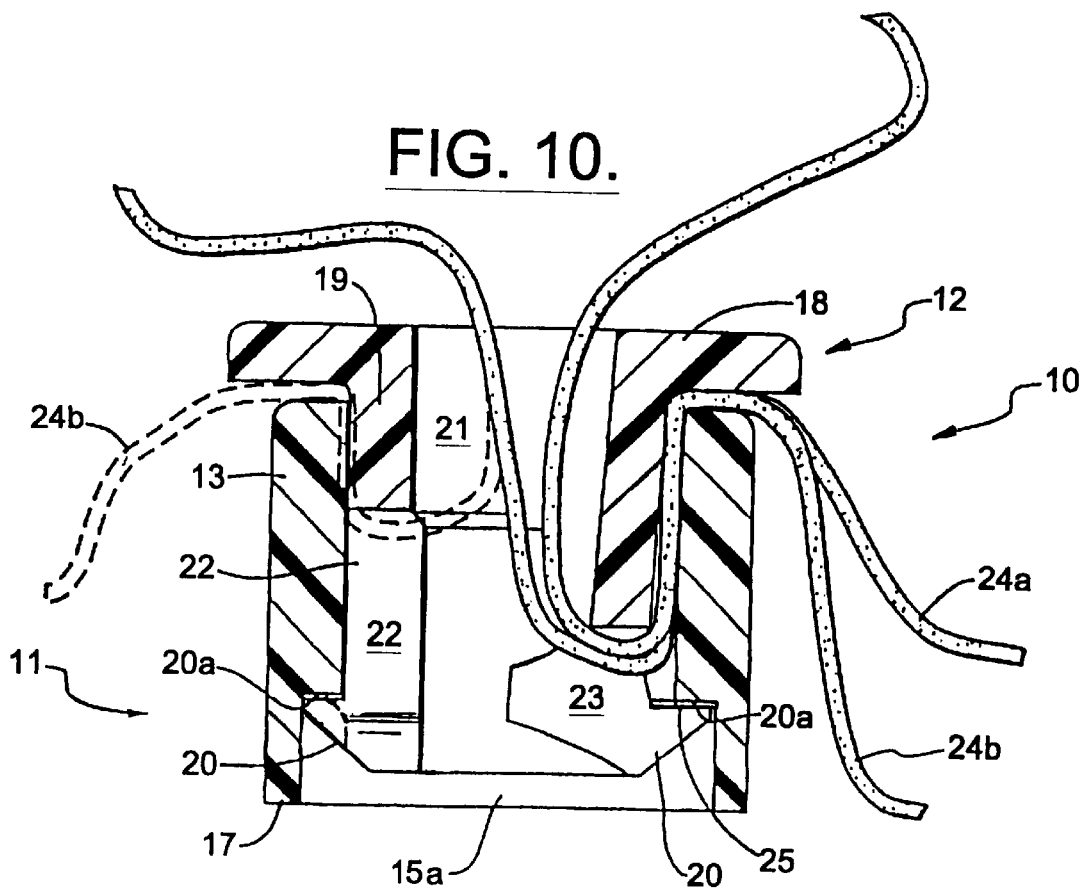
FIG. 10 is an enlarged sectional view like that of FIG. 9, showing the inner member as having passed into the outer member and showing two suture strands having passed out of the inner member round side hole and having traveled together along the inner and outer member opposing or shared surfaces to extend out from the outer member end.

In FIG. 10 the inner member 12 has been axially snap fit into the outer member 11, breaking the junction 20b shown in FIG. 9, and causing an elastic deformation of the outer member 11 as it travels over the inner member 12. Such deformation is within the elastic properties of the material from which the inner and outer members are manufactured. The suture strands 24a,24b are crushed between the shared or opposing member surfaces, locking the suture strands to the connector 10. The suture strands have been formed into a loop 24c, shown in FIG. 17, such as for fitting around a bone (not shown), and the suture strands can be separated and passed out of the round and elongate portals 23,22, respectively, as shown in FIG. 8.

Figure 11:
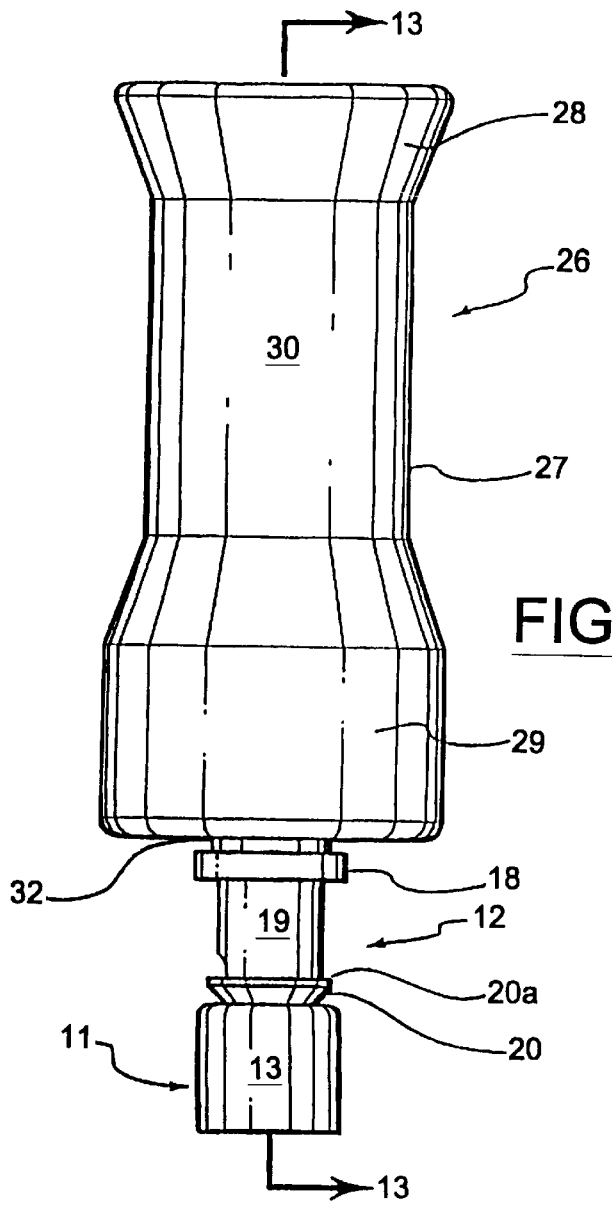
FIG. 11 is a side elevation view of a first embodiment of a one-piece breakaway connector device of the invention that includes a handle connected axially to an inner member that, in turn, connects axially to an outer member.
Figure 12A:
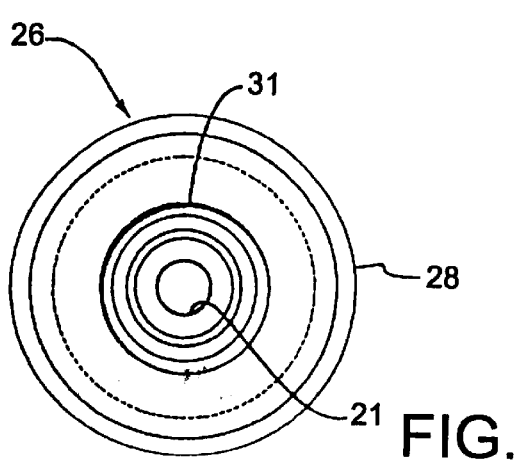
FIG. 12A is a top plan view of the handle and breakaway connector device of FIG. 11.
Figure 12B:
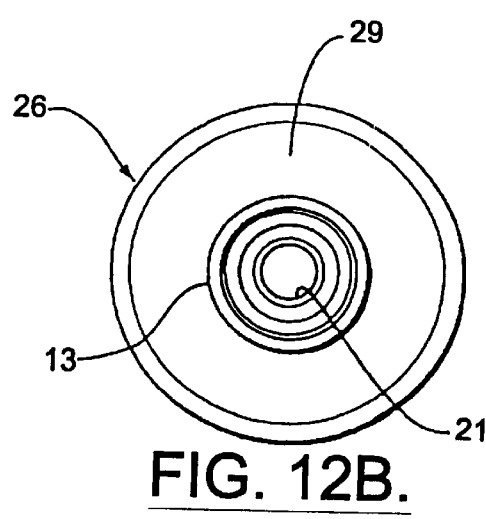
FIG. 12B is a bottom plan view of the handle and breakaway connector device of FIG. 11.
Figure 13:
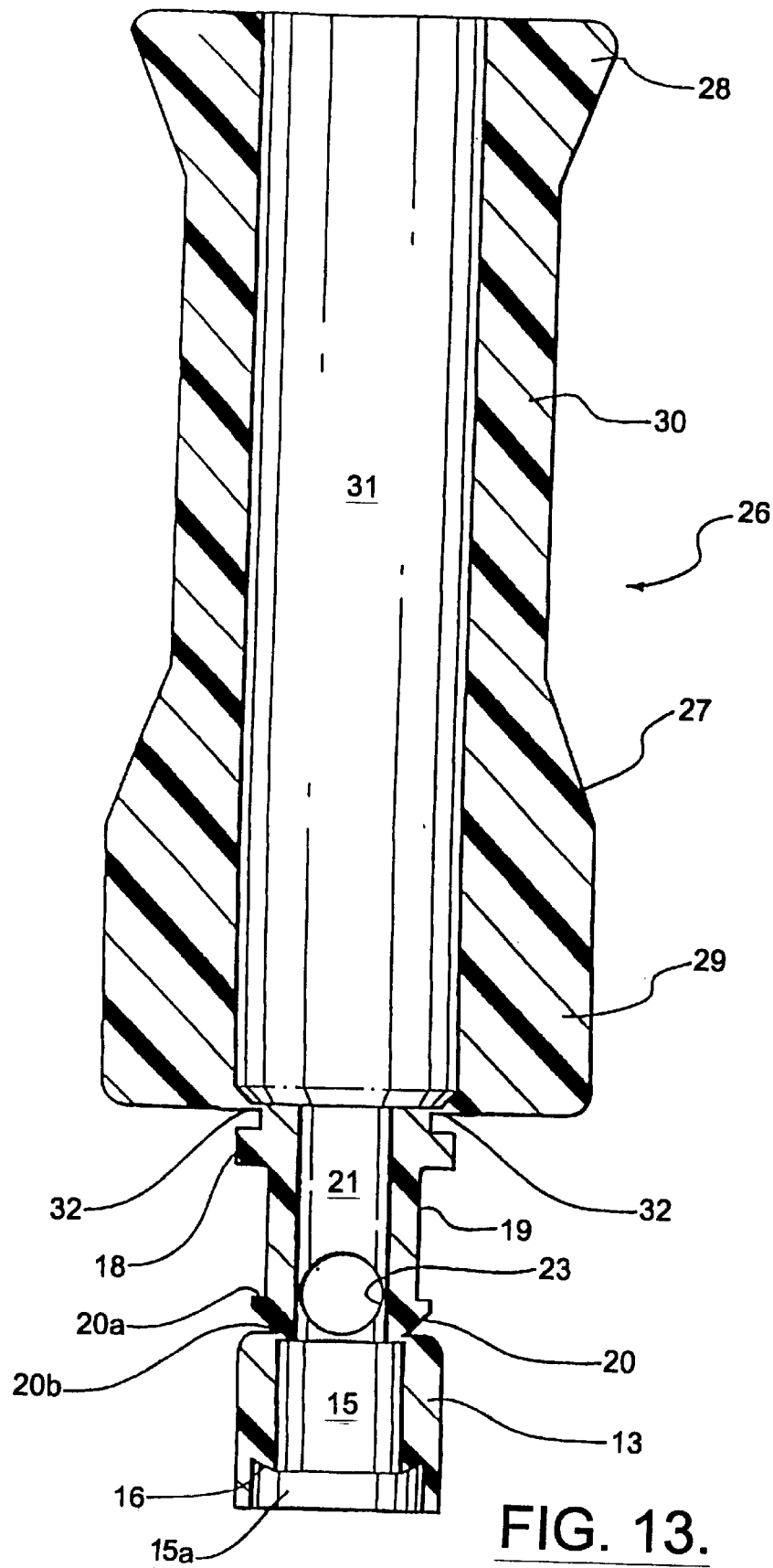
FIG. 13 is a longitudinal sectional view taken along the line 13—13 of FIG. 11.
Figure 14:
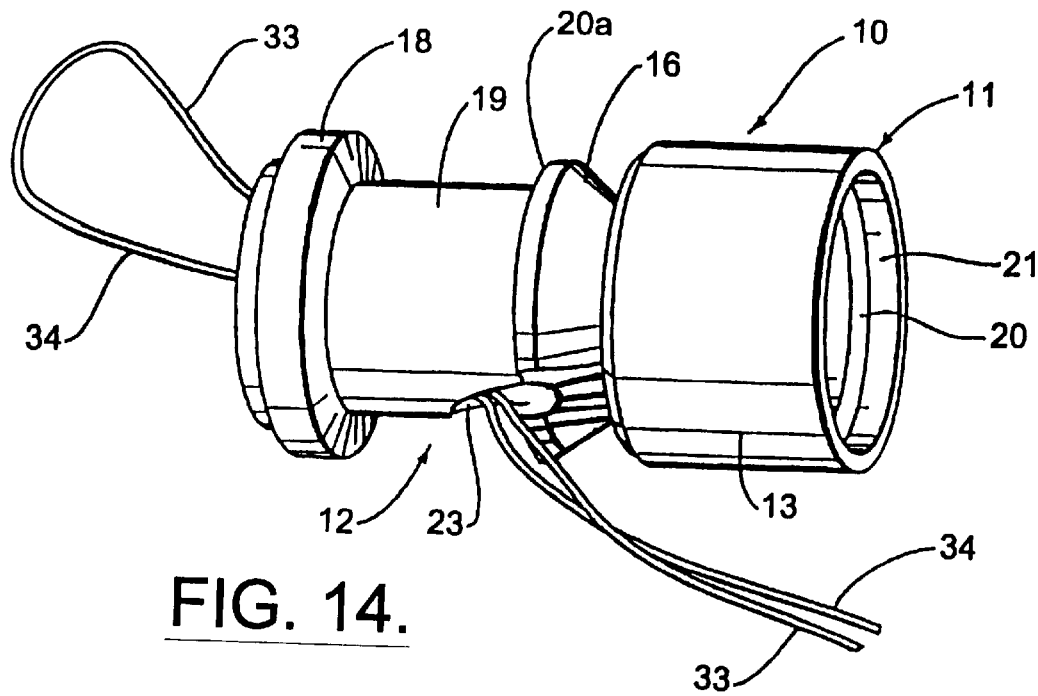
FIG. 14 is an enlarged view of a section of the breakaway connector device of FIG. 11, showing the inner member as having been separated from and having traveled into the outer member, and showing an adjacent portion of the handle before it is broken away.
Figure 15:
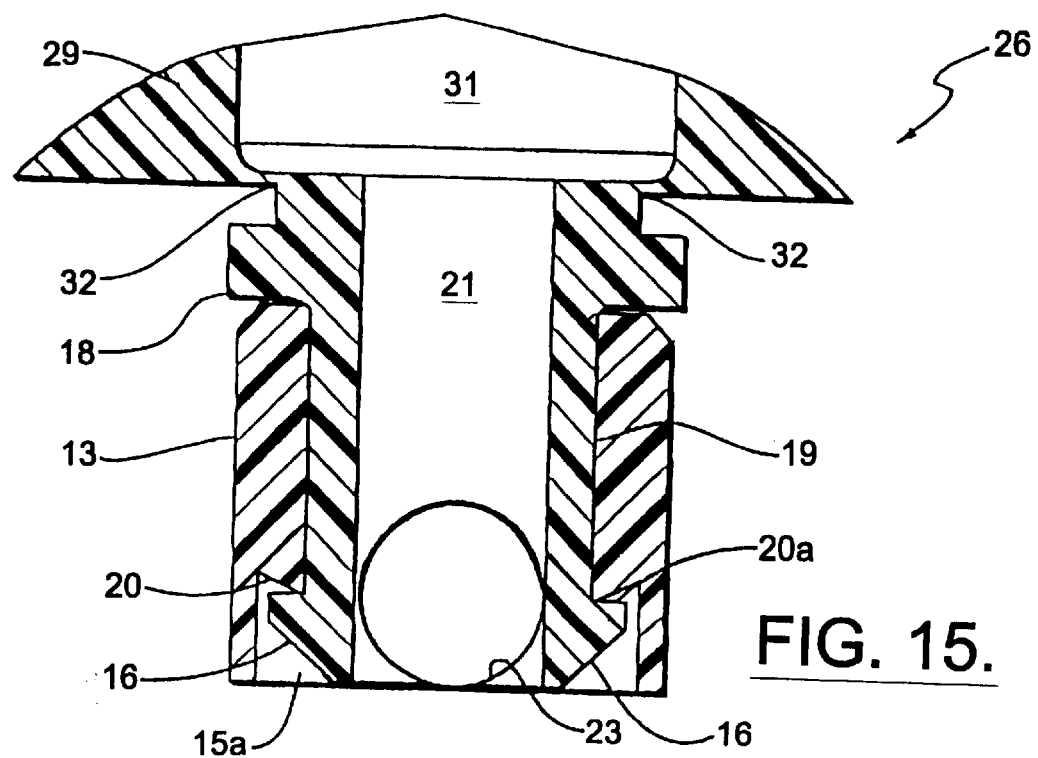
FIG. 15 is a side elevation perspective view of the inner and outer members of FIG. 11 less the handle and showing a suture formed into a loop with the two suture ends fitted through the inner member center passage and exiting an inner member side opening.

The connector 10 can, as discussed, be formed as inner and outer members 12,11, respectively, that are manufactured as single units to be broken apart when used and can, as shown in FIGS. 11 and 13, also include a handle 26, to facilitate loading the members into delivery instruments 35,75 to be described with respect to FIGS. 16–21. The handle 26, shown in FIGS. 11, 12A, and 12B, and in longitudinal section in FIG. 13, includes a body 27 that preferably has a cylindrical shape with greater-diameter top and bottom end portions 28,29, respectively, than a center portion 30, and includes an open center longitudinal bore 31 formed therethrough. It should be understood that the invention is not intended to be limited to any particular shape and/or arrangement of handle 26, with the cylindrical shape, as shown, being preferred only for convenience of manufacture. Any appropriate shape of handle 26 could be used providing for joining to the inner member top 18 at a thin section of material 32, shown best in FIG. 13. This coupling is formed to conveniently break when a side-to-side bending force is applied thereto, illustrated by arrow in FIG. 17. Such applied force separates the handle from the inner member top portion after the outer member 11 has been seated over the inner member 12, as shown in FIGS. 14 and 15.

Figure 17:
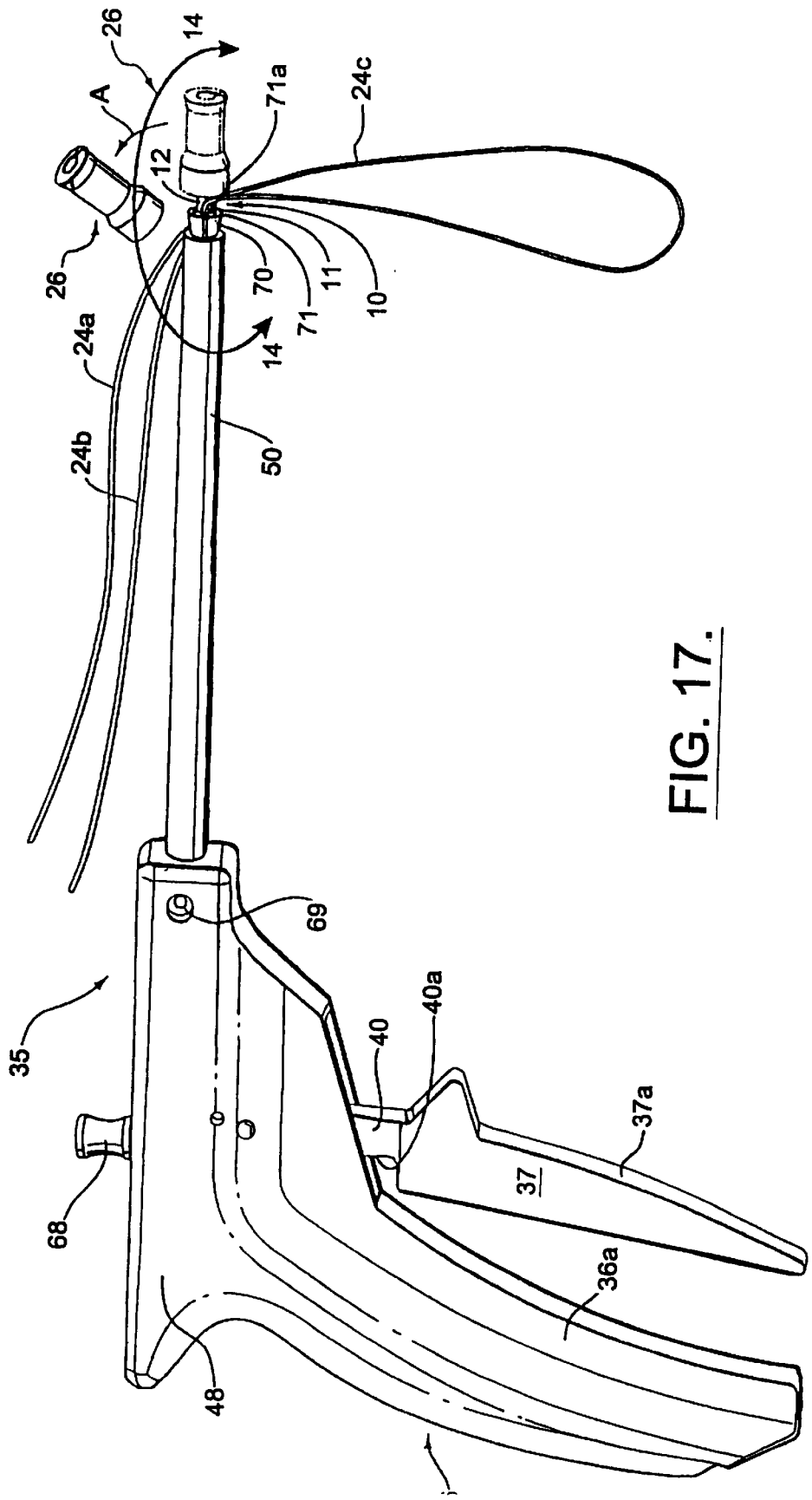
FIG. 17 shows the assembled delivery instrument of FIG. 16 with the connector device fitted into the outer tube end after strands of a suture that has been formed into a loop having been passed through the inner member longitudinal passage and out a side hole thereof and extend alongside of the delivery instrument outer tube, and showing, in broken lines, the inner and outer member as having been fitted into the outer tube and a handle broken away therefrom.

The connector 10 is shown in FIGS. 10 and 17 for use in joining strands 24a,24b of a single suture together that has been formed into a loop 24c, shown in FIG. 17. Also, it should be understood that the connector 10 is suitable for joining individual sections of material, such as sutures 33,34 shown in FIG. 15, wherein the material can be the same, such as sutures 33,34, or physically different, such as sutures, cable, wire, or even soft tissue, and the like, so long as they are individually flexible, within the scope of this disclosure.

A second embodiment of a delivery instrument 35 (FIGS. 16–18B) is for installing the breakaway connecting device 10 of FIGS. 11–14 onto a suture 24. Suture 24 is shown as having been formed into a loop 24c in FIG. 17 to deliver the connector 10 to a site or location in a human body. The suture strands 24a,24b are maintained alongside an instrument barrel 50 for pulling the suture loop 24c tightly around an item such as, but not limited to, a bone (not shown). The connector 10 is passed along the suture to the chosen connection site. The suture strands are then connected through the seating of the connecting device 10 inner member 12 in the outer member 11, as described previously.

Figure 16:
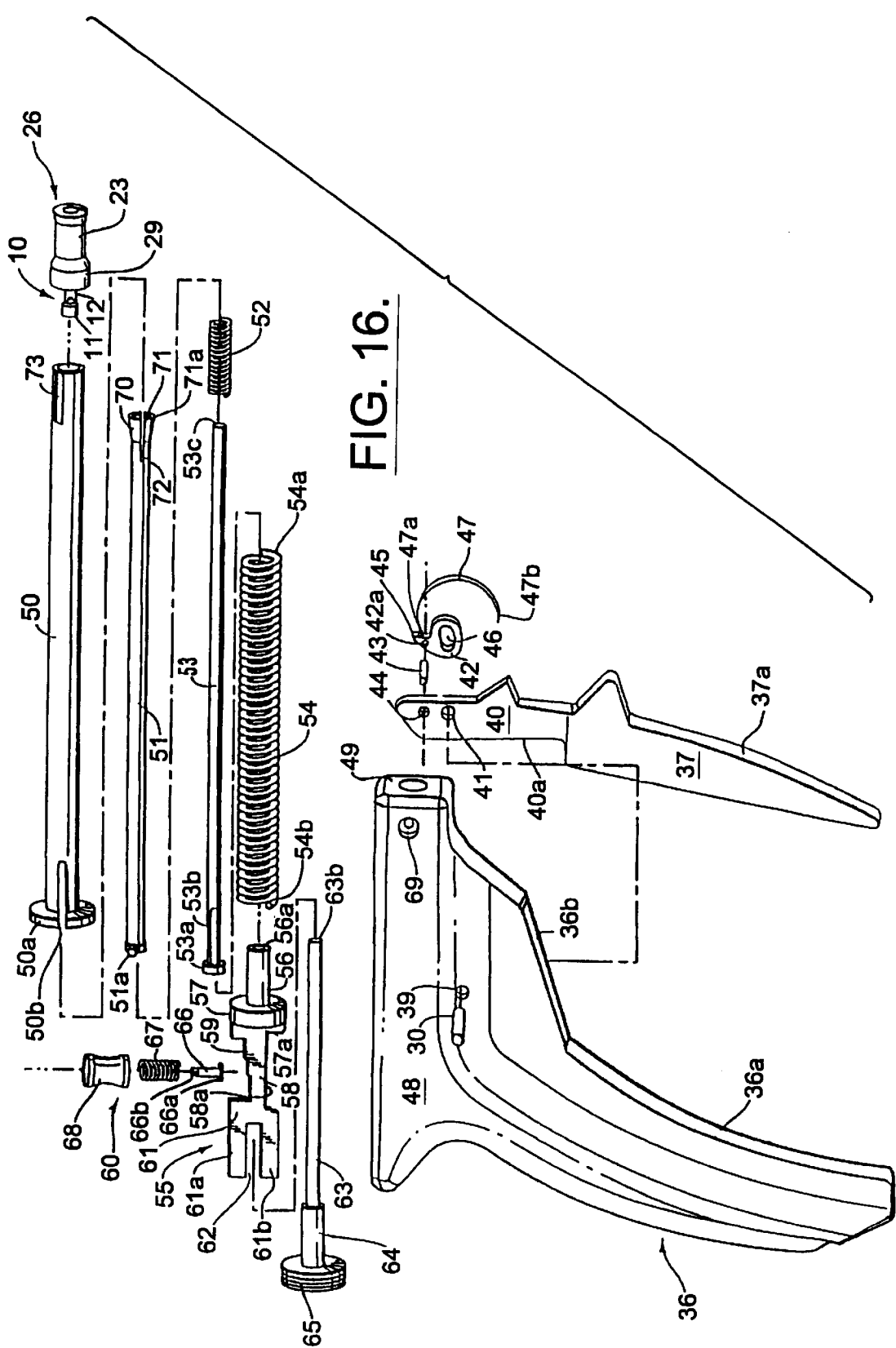
FIG. 16 shows an embodiment of a delivery instrument of the invention as it is used to deploy the connector device in an endoscopic procedure, showing the instrument component parts or elements exploded apart and showing the breakaway connector device of FIG. 11 aligned for fitting into an open end of an outer tube.

The delivery instrument 35, as shown best in the exploded view of FIG. 16, preferably includes a pistol grip handle 36 that is arranged for gripping by a user. A trigger 37 is pivotally mounted to the handle 36 by fitting a trigger pin 30 through a pair of holes 39 that have been formed through spaced sections 36b of the handle 36. A trigger top section 40 is slid between the spaced sections 36b. The trigger pin 30 passes through a hole 41 formed in the trigger top section 40, completing the pivotal mounting of the trigger 37 to the handle 36.

A pawl 42 is provided for mounting to the trigger top section 40 by fitting a pawl pin 43 through a hole 44 that has been formed through the trigger top section 40, above the trigger pin hole 41. The pawl pin 43 is also fitted through a pawl hole 45, with the trigger pin 30 also passing through an elongate pawl hole 46, for guiding pawl movement. The pawl 42 includes a curved leaf spring 47 that is secured at an end 47a to a pawl flat top portion 42a. Thus when the pawl 42 and trigger 37 are mounted to the pistol grip handle 36, as described, the surface of the pawl curved leaf spring 47 will fit against a straight rear face 40a of the trigger top section 40, biasing the trigger 37 away from a forward edge 36a of the pistol grip handle 36.

The spring biasing is overcome by a user squeezing the forward edge 37a of the trigger 37 to pull it toward the pistol grip handle 36. The trigger 37 operates the delivery instrument, as will be discussed below, and when the squeezing pressure to pull the trigger 37 toward the handle 36 is removed, an end 47b of the pawl curved leaf spring 47 will engage teeth 58a formed along a straight bottom surface of a center portion 58 of a driver. In that engagement, the pawl spring end 47b travels along the teeth 58a to provide a ratcheting action that, upon release of the trigger 37, is released with the trigger moving away from the pistol grip handle forward edge 36a.

A top section 48 of the pistol grip handle 36, as shown in FIG. 16, is open therethrough with a forward or proximal end thereof formed as a cylindrical opening 49 that has a diameter sufficient to pass an outer tube or barrel 50 therethrough, as shown in FIG. 17. The tube or barrel 50 passes along the cylindrical opening 49 to where a barrel collar end 50*a* engages the inner edge around opening 49, blocking further travel, with the tube or barrel 50 maintained in the opening 49 through the pistol grip handle 36 by turning a set screw, not shown, through a hole 69 formed through the top portion 48 that engages the barrel collar end 50*a*.

A collet tube 51 is provided for fitting into the barrel 50, and slides therein to where a pair of lugs 51*a* that are formed to extend outwardly from the collet tube distal end will pass into slots 50*b* that have been formed in the collet tube longitudinally from the barrel collar end 50*a*. A pusher rod biasing coil spring 52 is fitted into the barrel to engage the collar 50*a* end, contacting on one end the lugs 51*a* with a pusher rod 53 to be fitted through the collet tube 51.

A pusher rod coil spring 52 is maintained between the lugs 51*a* and an end collar 53*a* that is formed across the pusher rod distal end, the function of which pusher rod coil spring 52 will be described below.

A driver coil spring 54 is arranged for fitting in the pistol grip handle 36 top section 48 opening, shown in broken lines in FIGS. 16 and 17, with a proximal spring end 54*a* thereof engaging the surface of the barrel collar end 50*a*, and with the opposite distal spring end 54*b* to receive a cylindrical end 56 of driver 55 fitted therein. Thereby, the distal spring end 54*b* engages a flat forward surface of a driver collar 57 that is formed across a base of the cylindrical end 56. So arranged, the driver 55 disposed within the top section opening is biased by driver coil spring 54 away from the barrel collar end 50*a*. The driver coil spring 54 also acts upon the trigger portion, which includes a top forward edge 37*b* that is in contact with a rear surface 57*a* of the driver collar 57. Thereby, under an urging of the driver coil spring 54, the rearward travel of the driver 55 will also move the trigger portion 37 away from the pistol grip handle's forward edge 36*a*.

The driver's center portion 58, above the series of teeth 58*a*, is stepped at 59 to accommodate and function with a release pawl 60, as discussed below. A distal or rear portion 61 of the driver 55, as shown in FIG. 16, includes a center longitudinal groove 62 formed therein between straight legs 61*a*,61*b*.

A centering pin or rod 63, which has a sleeve 64 secured to its distal end, is positioned alongside the groove 62 of the assembled delivery instrument 35. A knob 65 is secured to the sleeve 64 distal end for gripping by an operator, with the center ring pin or rod 63 fitted, at its proximal end 63*a*, through the driver collar 57 and tube end 56 and is secured in the pusher rod's longitudinal passage 53*b*, shown in broken lines, formed in the pusher rod 53 distal end. So arranged, with the delivery instrument 35 assembled, as shown in FIG. 17, the centering pin or rod's sleeve 64 is positioned to be guided to travel back and forth along the driver slot 62 to move the pusher rod 53 back and forth, as will be discussed below.

The release pawl 60 allows the driver 55 to travel forward to where the driver's cylindrical end's forward surface 56*a* engages and pushes against the biasing of spring 52, extending the push rod's end 53*c* against lug ends 51*a*. To provide this release, the release pawl 60 includes a straight rod 66 that includes a disk 66*a* secured across its lower end and is fitted through a release pawl coil spring 67. The straight rod 66 receives a knob 68 secured across its top end as by turning a set screw, not shown, through a threaded hole formed in knob 68, not shown, that is turned into a set screw hole 66*b* formed in the straight rod 66 top end. In the assembly of release pawl 60, the straight rod 66 is fitted through the release pawl coil spring 67 and is then passed through a hole formed in the surface of the pistol grip handle's top section 48, with the knob 68 attached thereto, above top section 48, as shown in FIG. 17.

Figure 18A:
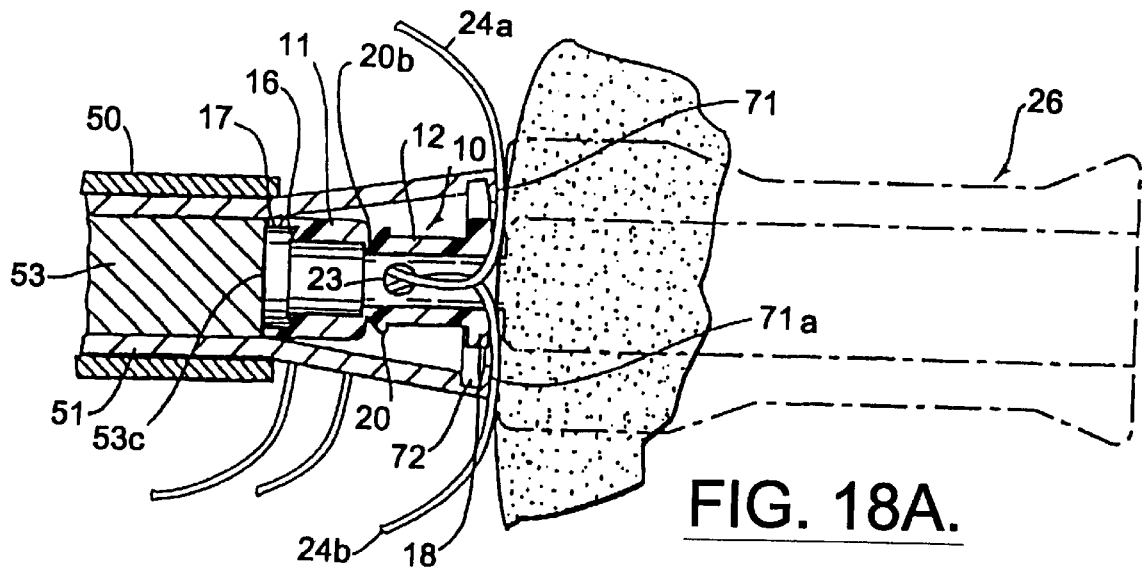
FIG. 18A shows an expanded sectional view taken within the line 18—18 of FIG. 17, showing in solid and broken lines the connector device maintained in a collet secured to the end of the delivery instrument collet tube, showing the inner member maintained in the collet with the outer member being urged thereover by operation of an instrument pusher rod and showing the pair suture sections folded upon themselves so as to pass between the opposing or shared surfaces of the inner and outer members.
Figure 18B:
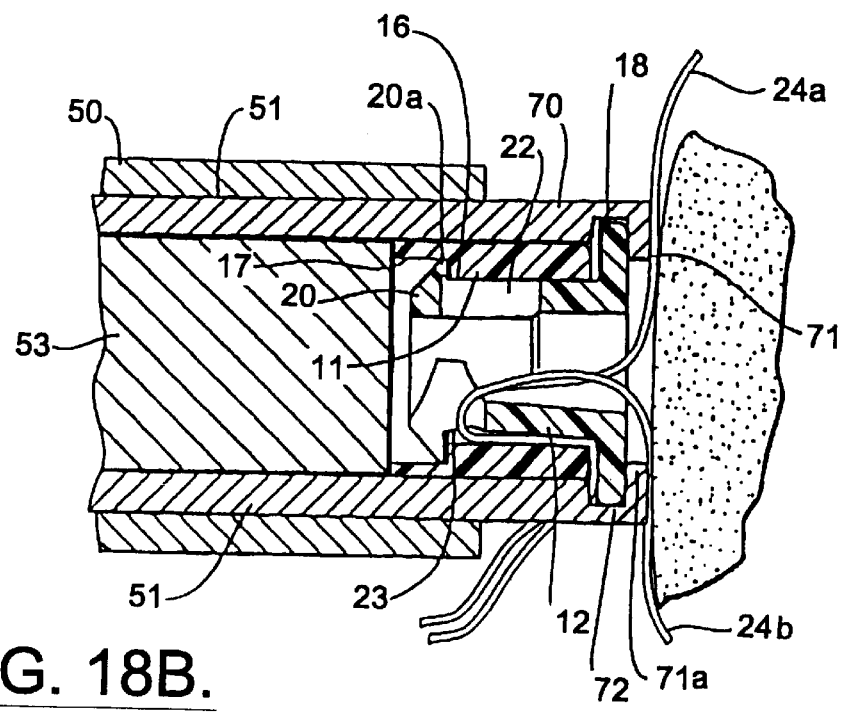
FIG. 18B is a view like that of FIG. 18A, after the outer member has been fully seated over the inner member with the flexible members, shown as suture sections, having passed into a longitudinal notch or slot that is formed in the delivery instrument outer tube.

As shown in FIG. 16, the collet rod 51 is ultimately movable by a user, not shown, holding the grip handle 36, who, by pulling or moving the trigger 37 to engage the grip handle leading edge 36, moves the push rod 53 to urge the outer member 11 over the inner member 12, as shown in FIGS. 18A and 18B. In this operation, a collet end 70, shown as a cone segment that is secured to the collet rod 51 forward or proximal end, holds the inner member therein by an engagement of an inturned lip 71*a* formed around the collet 70 cone base 71 with a top edge of the inner member's top 18.

The junction 20*b*, shown in FIG. 18A, between the delivery device 10 outer and inner members 12,11, is broken as the push rod's end 53*c* engages the outer member end 17 and forces it upwardly to where it passes over the inner member frustrum cone 20 bottom portion, the cone edge seating in the outer member's inwardly stepped flat section 16, as shown in FIG. 18B. The outer member 11 is thereby passed along the inner member (FIG. 18), compressing suture sections 24*a*,24*b* between the shared or opposing member surfaces. The collet end 70, as shown, is open across cone base at 71, which is flared inwardly into a lip 71*a* and includes a plurality of longitudinal slots 72 formed from that base extending into the collet rod. The slots 72 allow the collet end to open, as shown in FIG. 18B, to release the engagement of the cone base lip 71*a* from the inner member's top 18 edge, allowing the further travel of the push rod 53 out from the barrel 510 open end. The collet end 70, as shown, is arranged within and to extend just beyond the barrel 50 at its proximal end and is to receive and seat therein the connected inner and outer members 11,12 of the breakaway connector device 10 of FIGS. 9 and 12.

Accordingly, as shown in FIG. 17, after the breakaway handle 26 of FIG. 12 is separated, as by rotating it away from the inner member's top end 18, illustrated by arrow A in FIG. 17, the user inserts the barrel into a site where flexible members are to be joined. Thereat, the user, by pulling the delivery instrument's trigger 37, as described above, both urges the outer member 12 over the inner member 11, and with continued trigger 37 travel towards handle 36 ejects the connected inner and outer members from the barrel 50 end with the suture strands 24*a*,24*b* locked between the inner and outer member shared or opposing surfaces. Suture strands 24*a*,24*b*, locking to the connecting device 10 shown in FIG. 17, are passed into a slot 73 that is formed longitudinally into the barrel, from the barrel proximal end. Optionally, the slot 73 can include a sharp edge whereby, with the suture strands 24*a*,24*b* held tightly by the user, the barrel 50 can be turned, as shown in FIG. 18B, to where the slot 73 sharp edge engages and cuts through the suture strands that are then removed.

Figure 19:
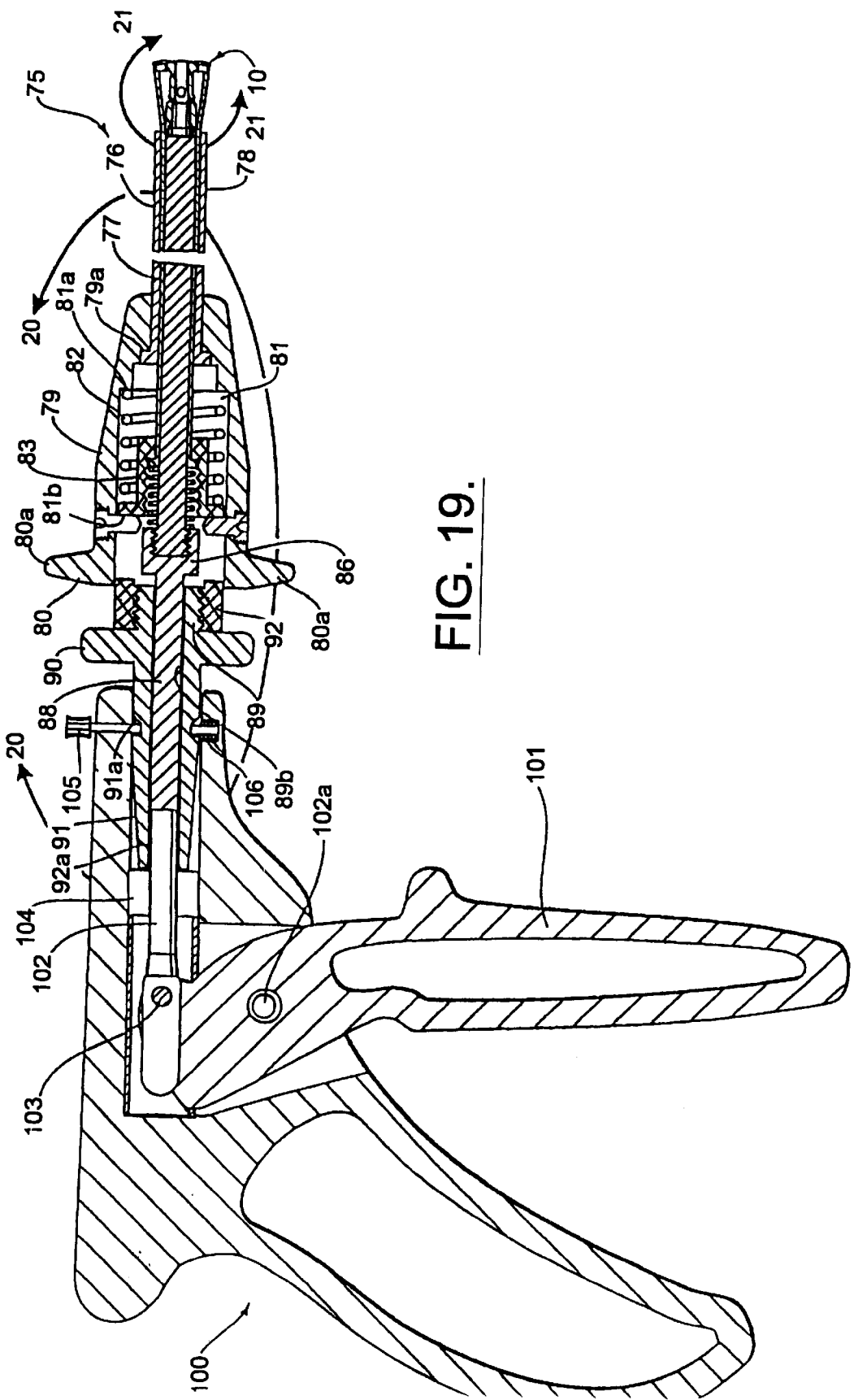
FIG. 19 is an assembled longitudinal sectional view of a second embodiment of a delivery instrument of the invention in use to deploy the connector device in an endoscopic procedure, the instrument including a handle with a trigger-operated plunger separated from a connector end of a body and showing the breakaway connection device of FIG. 11 therein.

FIGS. 19 and 20 show a second embodiment of a delivery instrument 75 of the invention that, while it is structurally different, is functionally similar to delivery instrument 35. Delivery instrument 75 is shown assembled in FIG. 19 and includes a body portion 76 maintained at its proximal end 91 in a handle 100. The delivery instrument 75 includes an outer tube or barrel 76, a collet tube 77, and a pusher 78, shown as a straight rod. Collet tube 77 is for receiving the connector 10 of FIGS. 9 and 12. The inner member 12 of connector 10 is inserted into the outer member 11 when the pusher 78 is urged through the collet tube 77 during operation. The outer member 11 is seated within the inner member 12, with the top 18 edge maintained by a lip 77b of a collet end 77a of the collet tube 77, as shown in the enlarged sectional view of FIG. 21.

Shown in FIG. 19 and in the enlarged view of FIG. 20, the delivery instrument 75 includes a body 79 having a forward or distal end, wherein is formed a longitudinal center bore that is stepped at 79a to receive a collar end 76a of the outer tube or barrel 76. A pull 80 is positioned distal of a body distal end 79a and includes an outer ring 80a formed therearound. A body cavity 81, which is a cylindrical opening formed within the body 79, is stepped inwardly at 81a and opens through a distal end at center opening 79a.

The body cavity 81 is open at a rear or proximal end 81b into an opening through the divider insert 80 and wherein a collet coil spring 82 is contained. The collet spring 82 rearward of distal end 82a engages the stepped end 81a of the body cavity 81 and has a rearward cylindrical end of a collet stop 83 fitted into its opposite or proximal end. A forward or distal end surface of the collet stop cylindrical end includes a hole 83a formed therein. The hole 83a is stepped outwardly at 84 to receive a collar end 77a of the collet tube 77 fitted therein and has a rear end that is formed into a flange 83b to engage and act as a stop for the collet coil spring 82. The collet stop 83, as shown in FIG. 20, is itself a cylinder, with the threaded hole 83a and outward step 84 formed in its rearward end and includes a center cavity 84a proximally therefrom containing a distal portion of a pushing rod coil spring 85. Set screws 179, set into the body 79 distal of pull 80, bear against the collet stop 83 proximal end for retaining the pushing rod coil spring in place. Set screws 179 are driven by drivers 179a.

The push rod 78 has its proximal end portion fitted through the coil spring 85 and connects by turning a threaded end 78a into a threaded hole 87. Hole 87 is formed into a distal end 86a of a pusher rod coupling collar 86, which is secured to a distal end of a pusher rod extension 88, which is fitted to slide through a longitudinal opening 89b formed through a pusher rod guide 89. The push rod guide 89 is turned at threaded section 89a into a sleeve 92 that is itself turned onto a threaded end 80b of the grip end 80. Push rod guide 89 includes an outwardly projecting ring flange 90 formed therearound that can be gripped by a user for guiding the device in the operation with the other hand gripping the handle 100 and pulling trigger 101 (FIG. 19). The push rod extension 88 is fitted to slide in a longitudinal passage 92a of a handle mount 91. An operator moving the handle 100 trigger 101 extends a pin 102 that engages and moves the push rod extension 88 and connected push rod 78 for operating the delivery instrument 75.

In operation, the outer member 11 of a connecting device 10 is seated over the inner member 12, as described with respect to the operation of delivery instrument 70 (FIGS. 18A and 18B), with the connected members then ejected from the outer tube or barrel 76. This causes the outer member 11 to pass over the inner member 12, whereby the flexible material is compressed between the connector's shared or opposing surfaces.

Loading the device 75 is accomplished by fitting the connected inner and outer members into the collet end 77a of the collet tube 77, a collet end inturned lip 77b engaging a top edge of inner member 12 top 18 (FIG. 21). When the delivery instrument 75 is operated, the outer member 11 is forced over the inner member 12, and the coupled members are then ejected out of the barrel 76 end. During delivery the ring-shaped outer member 11 is separate from and travels over the inner member 12.

Push rod 78 extension is provided by a user, who holds the handle 100 and squeezes the trigger 101. The handle 100 (FIG. 19) connects at a distal end to handle mount 91 of the body 79 by lifting a button 105 end of a rod 106 that is spring biased to fit into a handle mounted slot 91a. So arranged, release of the button 105 allows the rod 106 to seat in slot 91a, connecting the handle 100 thereto. The trigger 101 is mounted to the handle by a pivot 102a such that, with the trigger squeezed, a rod 102 mounted to the trigger end at 103 will be urged through a sleeve guide 104 to extend into longitudinal passage 92a of the handle mount 91. The rod 102 end thereby engages and moves the push rod extension 88. As with the delivery device 35, with the ejection of the connector 10, the suture strands 24a,24b (FIGS. 18A and 18B) are preferably cut close to the connecting device. Thereafter, the cut suture strands are removed.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A device for delivering a connector to a surgical site, the connector comprising a generally cylindrical inner member adapted to move from an open position to a locked snap fit position within a bore of a generally cylindrical outer member for trapping flexible material therebetween, the device comprising:

a rod frangibly affixed at a top end to a bottom end of the inner member having a diameter adapted to slide within a bore of the outer member, the rod for retaining the inner member stationary while the outer member is moved upward to force the inner member into the locked position;

a support member having:
  a longitudinal bore extending from a top end to a bottom end and having a diameter dimensioned to permit the rod to slide therewithin; and
  means adjacent the top end for supporting the outer member in a fixed location relative thereto;
wherein a sliding of the support member upward relative to the rod achieves a movement of the inner member into the locked position and further breaks the rod away from the inner member; and
a driver body comprising:
  a handle having a passage therethrough;
  an outer cylinder kinetically coupled to the support member bottom end;
  an inner cylinder positioned within the outer cylinder and kinetically coupled to a top of the handle and to the bottom end of the rod; and means for moving the outer cylinder axially relative to the handle, the moving means movably positioned within the handle passage and kinetically decoupled from the inner cylinder;

wherein an upward movement of the moving means relative to the handle causes the outer member to be moved upward and form the locked position with the inner member.

2. A device for delivering a connector to a surgical site, the connector comprising a generally cylindrical inner member adapted to move from an open position to a locked snap fit position within a bore of a generally cylindrical outer member for trapping flexible material therebetween, the device comprising:

a rod frangibly affixed at a top end to a bottom end of the inner member having a diameter adapted to slide within a bore of the outer member, the rod for retaining the inner member stationary while the outer member is moved upward to force the inner member into the locked position, the rod further having a threaded screw section adjacent a bottom end adapted to mate with a stationary, correspondingly dimensioned grooved section on the stationary portion of a driver for permitting remote relative movement therebetween, for achieving the locking position; and a support member having:
 a longitudinal bore extending from a top end to a bottom end and having a diameter dimensioned to permit the rod to slide therewithin;
 means adjacent the top end for supporting the outer member in a fixed location relative thereto; and
 a grooved section within the bore adjacent the bottom end adapted to mate with a movable, correspondingly dimensioned threaded screw section of a driver;

wherein a sliding of the support member upward relative to the rod achieves a movement of the inner member into the locked position and further breaks the rod away from the inner member.

3. A device for delivering a connector to a surgical site, the connector comprising a generally cylindrical inner member adapted to move from an open position to a locked snap fit position within a bore of a generally cylindrical outer member for trapping flexible material therebetween, the device comprising:

a rod frangibly affixed at a top end to a bottom end of the inner member having a diameter adapted to slide within a bore of the outer member, the rod for retaining the inner member stationary while the outer member is moved upward to force the inner member into the locked position; and a support member having:
 a longitudinal bore extending from a top end to a bottom end and having a diameter dimensioned to permit the rod to slide therewithin; and
 means adjacent the top end for supporting the outer member in a fixed location relative thereto;

wherein a sliding of the support member upward relative to the rod achieves a movement of the inner member into the locked position and further breaks the rod away from the inner member.

4. The device recited in claim 3, wherein the rod has a means for mating with a stationary portion of a driver.

5. The device recited in claim 4, wherein the mating means comprises a threaded screw section adjacent a bottom end adapted to mate with a correspondingly dimensioned grooved section on the stationary portion of the driver.

6. The device recited in claim 5, wherein the rod further has a groove extending from the top end, the groove in communication with an exit portal on the inner member for passing flexible material therethrough and dimensioned to permit the piece of material to reside therein, the groove for facilitating a loading of the piece of material onto the connector with the inner member in the open position.

7. The device recited in claim 5, wherein the rod has a diameter adapted to engage at least a portion of the outer member bore sufficiently closely to retain the outer member in position adjacent the inner member bottom end prior to moving the connector into the locked position.

8. The device recited in claim 3, wherein the support member further has means adjacent the bottom end for mating with a movable portion of a driver and the rod further has means adjacent a bottom end for mating with a stationary portion of the driver for permitting remote relative movement therebetween, for achieving the locking position.

9. The device recited in claim 8, wherein the rod mating means comprises a threaded screw section adjacent the bottom end adapted to mate with a correspondingly dimensioned grooved section on the stationary portion of a driver.

10. The device recited in claim 9, wherein the support member mating means comprises a grooved section within the bore adjacent the bottom end adapted to mate with a correspondingly dimensioned threaded screw section on the movable portion of the driver.

11. The device recited in claim 3, wherein the support member bore has a widened section having a diameter greater than a bore diameter therebeneath, the widened section adjacent the top end dimensioned and adapted to permit the outer member to reside therein, the support means thereby comprising the bore widened section.

12. The device recited in claim 3, further comprising a driver body comprising:
 a handle having a passage therethrough;
 an outer cylinder kinetically coupled to the support member bottom end;
 an inner cylinder positioned within the outer cylinder and kinetically coupled to a top of the handle and to the bottom end of the rod; and
 means for moving the outer cylinder axially relative to the handle, the moving means movably positioned within the handle passage and kinetically decoupled from the inner cylinder;

wherein an upward movement of the moving means relative to the handle causes the outer member to be moved upward and form the locked position with the inner member.

13. The device recited in claim 12, wherein:
 the inner cylinder has a pair of radially opposed axial slots therein;
 the moving means comprises a plunger element having a widened portion adapted to slide within the inner cylinder slots and a rod portion narrower than the widened portion extending downward from the widened portion into the handle passage, the rod portion movable by a push rod inserted into a bottom end of the handle passage.

14. A method for delivering a connector to a surgical site, the connector comprising a generally cylindrical inner member adapted to move from an open position to a locked snap fit position within a bore of a generally cylindrical outer member for trapping flexible material therebetween, the method comprising the steps of:

providing a rod frangibly affixed at a top end to a bottom end of the inner member having a diameter adapted to slide within a bore of the outer member, the rod for retaining the inner member stationary while the outer member is moved upward to force the inner member into the locked position; and supporting the outer member on a support member, the support member having a longitudinal bore extending from a top end to a bottom end and having a diameter dimensioned to permit the rod to slide therewithin;

sliding the support member upward to move the inner member into the locked position.

* * * * *